(12) United States Patent
Sage, Jr. et al.

(10) Patent No.: US 6,584,349 B1
(45) Date of Patent: *Jun. 24, 2003

(54) LOW COST ELECTRODES FOR AN IONTOPHORETIC DEVICE

(75) Inventors: Burton H. Sage, Jr., Raleigh, NC (US); John R. DeNuzzio, Chapel Hill, NC (US); C. Randolph Bock, Durham, NC (US); John L. Haynes, Chapel Hill, NC (US); Vilambi Reddy, Bloomingdale, NJ (US)

(73) Assignee: Vyteris, Inc., Fair Lawn, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/971,458

(22) Filed: Nov. 17, 1997

Related U.S. Application Data

(63) Continuation of application No. 08/536,029, filed on Sep. 29, 1995, now abandoned.

(51) Int. Cl.[7] .................................. A61N 1/30
(52) U.S. Cl. .......................... 604/20; 604/20
(58) Field of Search ............................ 604/20–21, 501; 607/115; 128/639

(56) References Cited

U.S. PATENT DOCUMENTS

| | | | |
|---|---|---|---|
| 4,141,359 A | | 2/1979 | Jacobsen et al. |
| 4,325,367 A | * | 4/1982 | Tapper |
| 4,619,252 A | * | 10/1986 | Ibbott |
| 4,764,164 A | | 8/1988 | Sasaki |
| 4,820,263 A | | 4/1989 | Spevak et al. ................. 604/20 |
| 4,927,408 A | * | 5/1990 | Haak et al. |
| 5,057,072 A | * | 10/1991 | Phipps |
| 5,084,008 A | * | 1/1992 | Phipps |
| 5,160,316 A | | 11/1992 | Henley |
| 5,246,417 A | | 9/1993 | Haak et al. |
| 5,312,326 A | | 5/1994 | Myers et al. |
| 5,320,731 A | * | 6/1994 | Muller et al. |
| 5,466,217 A | | 11/1995 | Myers et al. |
| 5,573,503 A | * | 11/1996 | Untereker et al. |

FOREIGN PATENT DOCUMENTS

| | | |
|---|---|---|
| EP | 0 182 520 | 5/1986 |
| GB | 410009 | * 5/1934 |
| GB | 2239803 | * 7/1991 |
| GB | 2 265 088 A | 9/1993 |
| WO | WO 90/04433 | 5/1990 |
| WO | WO 95/27258 | 10/1995 |

* cited by examiner

Primary Examiner—Mark Bockelman
(74) Attorney, Agent, or Firm—Kirkpatrick & Lockhart LLP

(57) ABSTRACT

The present invention claims an apparatus for transdermal delivery of medicaments, with novel electrode systems, which avoids burns caused by changes in pH or excessive current applied at the sight of delivery, which is low in cost and easy to manufacture. In the present invention, preferably, the anode of the electrode system is predominantly formed from a low-cost bulk base metal which includes a coating of a precious metal thereon. The cathode of the electrode system is preferably formed from an chemically inert material which is a poor electron condutor and is coated on a good electron conductive material which has poor chemical stability. The electrode system of the present invention is highly efficient, easy to manufacture and cost-effective.

77 Claims, 17 Drawing Sheets

LOW COST ELECTRODES FOR AN IONTOPHORETIC DEVICE

This application is a continuation of application Ser. No. 08/536,029, filed Sep. 29, 1995 now abandoned.

BACKGROUND OF THE INVENTION

1. Field of the Invention

The present invention generally relates to iontophoretic devices for delivery of drugs or medicines to patients transdermally, i.e., through the skin, and more particularly relates to an iontophoretic drug delivery device having low-cost electrodes and which are easy to manufacture.

2. Background of the Invention

Iontophoretic drug delivery systems, have, in recent years, become an increasingly important means of administering drugs.

Presently there are two types of transdermal drug delivery systems, i.e., "passive" and "active." Passive systems deliver drug through the skin of the patient unaided, an example of which would involve the application of a topical anesthetic to provide local pain relief. Active systems, on the other hand, deliver drug through the skin of the patient through the application of an electromotive force (iontophoresis) to drive ionizable substances (medicament) into the skin so that they can be absorbed by adjacent tissues and blood vessels. Such systems offer advantages clearly not achievable by other modes of administration, such as hypodermic injection which has the associated problem of pain, risk of infection and trauma to the patient as well as avoiding introduction of the drug through the gastrointestinal tract which has problems of inactivation of the medicament.

Conventional iontophoretic devices, such as those described in U.S. Pat. No. 4,820,263 (Spevak, et al.), U.S. Pat. No. 4,927,408 (Haak, et al.) and U.S. Pat. No. 5,084,008 (Phipps), the disclosures of which are hereby incorporated by reference, provide for delivery of a drug or medicament transdermally through iontophoresis. Basically, conventional iontophoretic devices consist of a power source connected to two electrodes, an anode and a cathode, which are individually in ionic contact with an electrolyte or drug reservoir which is in contact with the skin to be treated by the iontophoretic device. When the current is turned on, electrical energy is used to assist in the transport of ionic molecules into the body through the skin, via ionic conduction.

Delivering drugs via iontophoresis was recognized long ago, however, due to several disadvantages and limitations the use iontophoretic drug delivery devices have not enjoyed widespread acceptance in the medical field. One reason is because a practical commercially feasible iontophoretic transdermal drug delivery device is still not available. Two major impediments with respect to iontophoretic devices are cost of manufacture and reliability. As previously noted, one problem encountered in the clinical use of transdermal drug delivery devices is that presently available devices have not been particularly economical. Generally, other methods of administration of medicaments have been less expensive and easier to use. Considerations such as cost, reliability and convenience have also impeded the general acceptance of transdermal drug delivery devices. Many iontophoretic systems include expensive electrode systems, such as Ag anode and AgCl cathode, electronic controls and sophisticated designs which are difficult to manufacture cost effectively.

One of the key components of an iontophoretic patch contributing to the high cost of the device is the electrode system. The problem of the high cost of the electrode system is particularly acute for electrodes being used for long duration iontophoresis (hours) and high current density (>50 $\mu A/cm^2$) applications. Accordingly, there is a need for an electrode system for an iontophoretic drug delivery device which would eliminate the problems and limitations associated with the prior devices discussed above, yet be easy enough to manufacture and also be cost-effective.

It is, therefore, an object of the present invention to provide an electrode system for an iontophoretic device which is inexpensive, easy to manufacture and reliable An electrode system as described herein may include the present inventions as described for the anode electrode, the cathode electrode or both, the anode and the cathode electrodes, of an iontophoretic electrode system.

It is a further object of the present invention to provide an electrode system for an iontophoretic device capable of producing high specific capacity, for example about 1 mA $hr/cm^2$ or greater.

It is yet a further object of the present invention to provide an electrode system for an iontophoretic device having good stability and a prolonged shelf-life.

It is yet a further object of the present invention to provide an electrode system for an iontophoretic device having the benefits of low voltage requirements thereby either eliminating or reducing demand on a system battery.

It is a further object of the present invention to provide a transdermal drug delivery device which utilizes cost-effective materials to form the electrode systems.

It is yet a further object of the present invention to provide a transdermal drug delivery device which is simple, convenient, and economical to manufacture and use.

SUMMARY OF THE INVENTION

These and other goals and objectives are satisfied, in accordance with the present invention, wherein one embodiment provides for an iontophoretic electrode assembly comprising an anode patch and a cathode patch.

The anode patch of the iontophoretic electrode assembly which includes an electrode compartment and a skin contact compartment which are in electrical (ionic) communication with one another. The electrode compartment includes an electrolyte and a metal electrode in electrical communication with the electrolyte. The present invention provides one embodiment in which the metal electrode further includes at least two electrochemically active dissimilar metals, such that a first metal provides a coating over a second metal. The coating, bonding and layering discussed herein with respect to the formation of the electrodes can be accomplished using methods known to those having ordinary skill in the art of making iontophoretic electrodes.

The two electrochemically active dissimilar metals form the metal electrode of the anode. An electrochemically active metal, is a metal which is capable of undergoing anodic dissolution (oxidation). Such metals include a bulk base metal, or a non-precious metal or metal composite which are good electron conductors but have limited, if any, chemical inertness. Such bulk metal would be coated with a dissimilar metal, namely, a precious metal or other chemically inert metal. The coating of precious metal (chemically inert metal) prevents the chemical reaction between the base metal and the electrolyte when the anode is in storage or otherwise not use. In this manner, shelf-life of the anode may be extended, while also significantly reducing the cost of manufacturing the electrode, since the electrode is mostly made of non-precious, usually low-cost bulk base metal. In a preferred embodiment, the metal electrode is fabricated substantially from copper, nickel, iron, aluminum, zinc or mixtures thereof which is coated with a layer of silver or other precious or chemically inert metal. An anode formed in accordance with the present invention has been found to exhibit good shelf-life stability as well as good voltage characteristics and stability over a prolonged period of usage in iontophoretic drug delivery devices. Furthermore, in satisfying the objects of the invention, the utilization of a base metal, such as copper, as the bulk material significantly reduces the cost of the anode.

Additionally, the anode of the present invention may be in a solid planar form, by way of example and not limitation, foil, laminates, printed ink on polymeric films and the like; or an open mesh form, by way of example and not limitation, woven, nonwoven screen, expanded foil and the like.

Most preferably the anode is fabricated from an expanded copper foil mesh which is treated with a silver coating. The copper foil mesh provides improved performance and reliability as demonstrated in the examples presented herein. Using silver as only a coating significantly reduces the cost and as the examples cited below demonstrate the electrodes of the present invention perform reliably. The metal electrode is contained in the electrode compartment in communication with the electrolyte.

Another embodiment of the present invention provides for the anode electrode to be formed from essentially one electrochemically active metal which a good electron conductor and chemically inert. By way of example only and not limitation aluminum may be used, since it has both characteristics. Additionally aluminum also reduces manufacturing costs and as the examples cited below demonstrate is reliable as an anodic electrode.

Details concerning some of the structure and function of portions of the iontophoretic device, namely, ion regulating means and compartment separation means, discussed herein below, are described more fully in a co-pending Application, U.S. Ser. No. 08/537,186, filed Sep. 29, 1995 entitled "Improved Iontophoretic Reservoir Apparatus", the disclosure of which is herein incorporated by reference.

Once the iontophoretic electrode assembly is in place on the patient and is activated the metal ions of the metal electrode become positively charged and move toward the skin contacting compartment. In order to keep the metal ions from reaching the skin, the anode may preferably include an ion regulating means which is in ionic communication with the electrolyte and metal electrode. The ion regulating means prevents electrochemically generated metal ions from migrating into the skin contacting compartment of the anode. The anode may also include a compartment separation means, preferably a size exclusion barrier situated between the metal electrode and the skin contacting compartment. The size exclusion barrier substantially prevents contact is of drug ions in the skin contacting compartment from migrating into the electrode compartment and contacting the metal electrode. Both the ion regulating means and size exclusion barrier may be in a variety of known forms and under specific circumstances the ion regulating means may also serve as a compartment separation means.

Another embodiment of the present invention is directed to a novel cathode patch of a patch for use in an iontophoretic electrode assembly. The cathode patch includes an electrode compartment and a skin contacting compartment electrically (ionic) connected to the electrode compartment. The electrode compartment includes an electrolyte containing a soluble, ionizable, reducible metal salt. Examples of such salts include but are not limited to chloride, nitrate and sulfate salts of copper, silver, zinc and iron. The electrode compartment further includes a cathode electrode in electrical communication with the soluble, reducible, ionizable metal salt.

The cathode patch of the present invention has two alternative embodiments with respect to the electrode compartment. In one embodiment, the electrode compartment of the cathode patch, is an electrode comprised of one material, which is both chemically inert as well as a good electron conductor. Such material may for example be precious metals such as platinum, gold, palladium and silver. However, silver is not chemically stable in metal chloride electrolytes (such as zinc chloride or copper chloride) and hence metal chloride salts must be avoided with silver as electrode material. However the use of such a single material may not serve to reduce the cost of manufacturing the device.

Another embodiment of the cathode patch of the present invention is a cathode comprised of a composite of two materials, a good chemically inert material, capable of limited conduction of electrons, in contact with the electrolyte on one side and on the other side in contact with a good electrically (electronic) conductive material, having limited or no chemical inertness. The coating, bonding and layering discussed herein with respect to the formation of the electrodes can be accomplished using methods known to those having ordinary skill in the art of making iontophoretic electrodes.

Additionally, the cathode of the present invention may be in a solid planar form, by way of example and not limitation, foil, laminates, printed ink on polymeric films and the like; or an open mesh form, by way of example and not limitation, woven, nonwoven screen, expanded foil and the like.

In a preferred embodiment, the material having good chemical inertness which by way of example and not limitation may be carbon, palladium, platinum, silver or gold or any other chemically inert material having the ability to conduct electrons. The chemically inert material is coated onto or bonded to any good electrically conductive material, for example, silver, copper, aluminum, zinc, iron, gold, platinum or a variety of known conductive polymers, conductive adhesives or conductive ceramics. Naturally if one trying to keep the cost of manufacturing down then gold and platinum would not be the electrically conductive materials of choice to use.

The cathode electrode compartment contains an electrolyte which has cations present in it for participation in the electrochemical reaction taking place at the cathode. In order to keep these cations from transporting away from the reaction cite and possibly into the skin contacting compartment, an ion regulating means may be used to separate the cathode electrode compartment and the skin contacting compartment, thus, keeping the cations in the cathode electrode compartment.

A complete iontophoretic drug delivery device contains an electrode assembly which comprises an anode patch of an iontophoretic device as described above in conjunction with the cathode patch of an iontophoretic device described above, such that in placing both anode and cathode patches against the skin of a patient completes an electrical circuit with an external power source for driving a medicament into the skin of the patient. As discussed above, iontophoresis involves the application of electric current to drive medicament ions into the skin of a patient. Accordingly, ions bearing a positive charge (placed in the anode skin compartment) may be driven into the skin at the anode of an electrical system and ions bearing a negative charge (placed in the cathode skin compartment) may be driven into the skin at the cathode of the electrical system. Preferred embodiments of the electrodes and a complete iontophoretic drug delivery device, as well as other embodiments, objects, features and advantages of this invention, will be apparent from the following detailed description of illustrative embodiments thereof, which is to be read in conjunction with the accompanying drawings.

DETAILED DESCRIPTION OF THE INVENTION

The present invention involves a low-cost, easy to manufacture, reliable electrode system for an iontophoretic device. The electrode system has the benefit of low voltage requirements thereby placing less demand on a system power source (battery). Additionally, the electrode systems of the present invention require no buffering since no proton electrochemistry or electrolysis of water is involved in the electrode reactions. Thus, there is no need to buffer against pH changes which can occur with some electrode systems presently being used.

Figure 1:
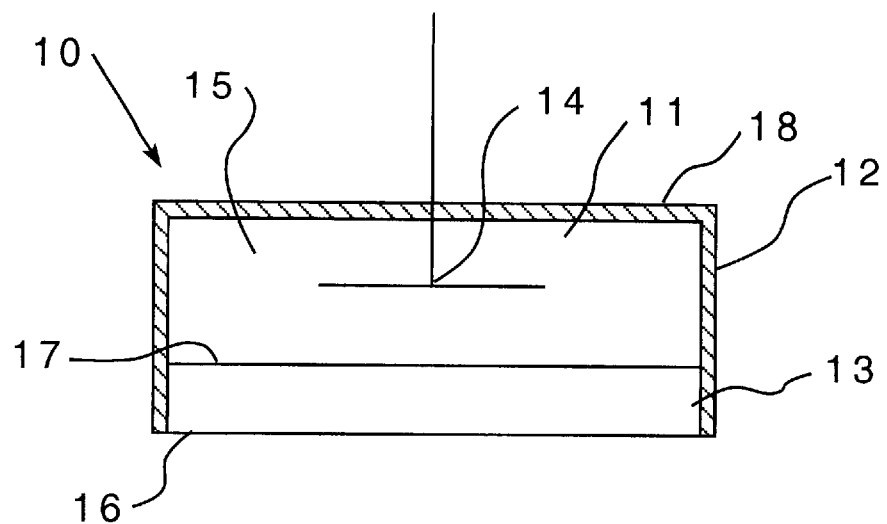
FIG. 1 is a cross-sectional view of an anode patch of the present invention.

FIG. 1 shows a cross-sectional view of an anode patch according to the present invention. The anode patch 10 is provided with a housing 12, which may be fabricated from an insulating material, such as a polymeric foam. Alternative housing materials include insulating plastics, such as polyvinyl chloride or polyethylene.

The anode patch includes an electrode compartment 11 which has electrolyte 15 and metal electrode or anode 14 in electrical communication with each other.

The anode 14 of the present invention can be any metal or metal composite which is capable of oxidation, i.e., $M \rightarrow M^{n+} + ne^-$. Suitable anode materials include, but are not limited to silver, iron, aluminum, tin, copper, zinc, nickel, aluminum, brass, metal alloys or mixtures thereof. To achieve the low cost iontophoretic device of the present invention, it is preferred that the bulk of the anode 14 be formed from a non-precious metal or metal composite. By using non-precious metals or metal composites such as aluminum, tin, zinc, copper, nickel, aluminum, brass, other metal alloys or mixtures thereof, significant cost savings as well as ease of manufacturing are achieved.

Figure 1A:
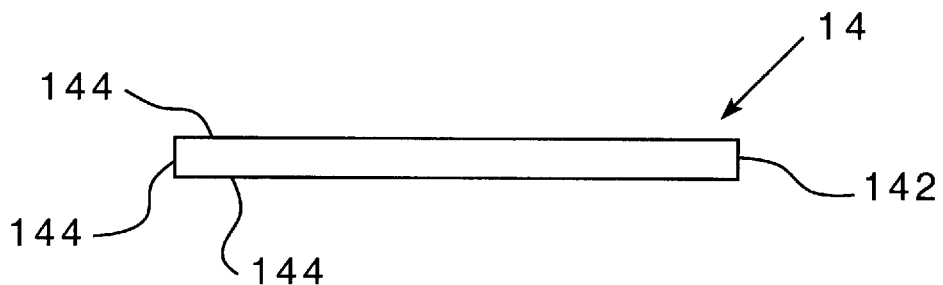
FIG. 1a is an exploded cross-sectional view of an anode electrode of the present invention which is comprised of two dissimilar metal.
Figure 1B:
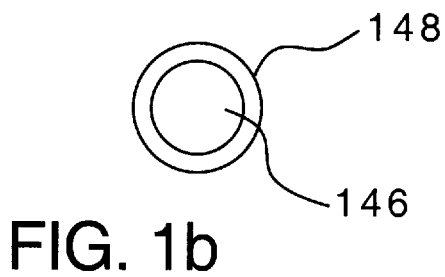
FIG. 1b is an exploded cross-sectional view of a strand of a mesh anode electrode of the present invention which is comprised of two dissimilar metals.
Figure 1C:
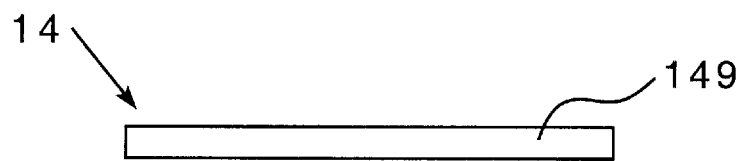
FIG. 1c is an exploded cross-sectional view of an anode of the present invention which is comprised of a single metal.

As described above and depicted in FIG. 1c, the anode 14 may be a single material 149, having both of the qualities desired, namely, good electron conductivity and good chemical inertness. Preferably as depicted in FIG. 1a, the anode 14 is a dual material electrode made from two dissimilar metals. More specifically, the anode comprises a bulk material, preferably an inexpensive, non-precious, base metal or metal composite described above 142 and a coating of a dissimilar metal, such as a precious metal 144. Preferably, as depicted in FIG. 1b, the anode 14 is formed by a bulk or base metal mesh 146 which is coated with a dissimilar precious or chemically inert metal 148. In a most preferred embodiment, the bulk of the anode is comprised of copper with a coating of a chemically, inert metal such as silver. The use of copper as a substantial part of the anode provides an effective, low-cost anode. The silver coating protects against the copper reacting with the aqueous salt environment of the electrolyte prior to use and provides stability to the anode to promote a longer shelf-life.

Additionally, the cathode of the present invention may be in a solid planar form, by way of example and not limitation, foil, laminates, printed ink on polymeric films and the like; or an open mesh form, by way of example and not limitation, woven, nonwoven screen, expanded foil and the like.

The anode described may be used as depicted in FIG. 1 in conjunction with an electrolyte 15 wherein the electrolyte is preferably a hydrogel matrix including saline and most preferably, containing a an ion regulating means. The ion regulating means is used to capture or repel metallic ions generated by the electrochemical anode reaction and prevent the metallic ions from transporting from the electrode compartment 11, into the skin contacting compartment 13. In an iontophoretic electrode of the invention, the ion regulating means is typically located between the electrode and the skin contacting compartment. For example, the ion regulating means may be located in the electrolyte reservoir, preferably near the site at which the reservoir apparatus would contact the electrode. By way of example, and not limitation, the ion regulating means may be located within the polymeric matrix of the electrolyte reservoir. In one preferred embodiment, the ion exchange material includes cation exchange resin distributed in the matrix of the electrolyte reservoir. In this embodiment, the spatial distribution of the ion exchange resin is desirably retained by the polymeric matrix. As a result, the ion exchange resin may be distributed in a discrete layer within the matrix of the electrolyte reservoir, Preferably as cationic exchange resins, particles or beads. Additionally the matrix may have resin particles or functional groups built in to the polymeric backbone of the matrix, thus creating a three dimensional ion regulating means. Alternatively, the ion regulating means may be an anion exchange membrane or film between the electrolyte reservoir and the anode skin contacting compartment which may be containing charged drug ions.

As mentioned above, an ion exchange membrane can also serve as the compartment separation means 17, preferably the selectively permeable membrane, if the electrolyte ions and drug ions can be separated on the basis of their charge characteristics. Therefore, a selectively permeable membrane composed of an ion exchange membrane 17 could be used to inhibit transport of species having a given ionic charge. By way of example and not limitation, an anion exchange membrane located between the anode electrode compartment and the skin contacting compartment will not only serve as an ion regulating means for preventing the transport of the metallic cations generated in the anodic electrochemical reaction as well as prevent the transport of the positively charged drug ions into the electrode compartment 11 from the skin contacting compartment 13 of the anode patch 10.

Once current is permitted to flow and the electrochemical reaction at the anode takes place, the silver coating is quickly exhausted, typically within 5–10% of the life of the electrode, by way of example and not limitation, for a 10 hour application, the coating is typically exhausted within 30–60 minutes of operation of the device. During that initial period in which the coating is the reactant, the primary reaction at the anode can be written as: $Ag \rightarrow Ag^+ + e-$. After the silver coating is used, the anode reaction is dominated by dissolution of copper as given by $Cu \rightarrow Cu^{+2} + 2e-$.

In a further preferred embodiment, the anode 14 is formed from a expanded copper foil mesh. An example of this material is manufactured by Delker Corp., Branford, Conn. The mesh electrode configuration provides greater surface area and access between the electrode and the electrolyte helping to improve performance and reliability. Accordingly, an improved voltage stability can be achieved by this electrode configuration. This type of electrode is illustrated in Example 1, below.

Referring back to FIG. 1, another embodiment of the anode patch 10, preferably includes a compartment separation means 17 positioned between the electrode compartment 11 and the skin contacting compartment 13, when the anode is being utilized to drive the drug into the patient's skin. The compartment separation means is preferably in the form of a size exclusion membrane, such as a YCO5 membrane manufactured by Amicon. The size exclusion membrane is selected to prevent the transport of the drug ions into the electrolyte matrix in the anode compartment. In this manner, the drug is maintained in the skin contacting compartment for delivery to the skin of a patient. Such an embodiment may, by way of example, include those in which the skin contacting compartment includes a solid, semi-solid material, polymeric film, semi-permeable for differentially permeable membranes or polycarbon and microporous membranes, all of which can be selected to suit the needs of the system.

The anode patch 10 may also include a suitable backing film 18 positioned on top of the electrode compartment 11. The backing film 18 provides protection against contamination and damage to the electrode compartment of the anode patch of the iontophoretic device.

The anode patch 10 optionally includes a release liner 16 which may be fixed to the underside of the skin contact compartment by an adhesive. The release liner 16 protects the skin contact compartment surface from contamination and damage when the device is not in use. When the device is ready for use, the release liner 16 may be peeled off to expose the skin contact compartment surface for application of the anode to a patient.

Another alternative embodiment of the anode, is fabricating the anode on a thin flexible polymeric film. The thin polymer film includes either a layer of a single metal described in FIG. 1c above or a layer two dissimilar metals as described in FIG. 1b, above bonded to the film material.

Printed ink technology can be used to form the electrodes of the present invention, as described in U.S. Ser. No. 08/012,168, filed Feb. 2, 1997 now abandoned, the disclosurue of which is herein incorporated by reference. Separate inks containing each of the desired materials would be formulated and separately applied. The ink may be applied to the polymeric film by techniques which include, but are not limited to, impression, lithography, offset, gravure, jet application, silk-screening and the like. Alternatively, the metal or metals forming the electrode may be applied to the polymeric film by electroplating, vacuum sputtering or any other method so that a uniform metallic layer is formed. Using printed ink technology a manufacturer may selectively pattern the shape and size of the electrodes and thus reduce cost and increase the ease of manufacturing.

As discussed above, and illustrated in FIG. 2b another preferred embodiment provides that the cathode may be fabricated from a single layer of material 243 which is both chemically inert electron conductor and an electrically conductive material (examples of which were provided above). The single layer of material may also be applied to a polymeric film 240 by techniques described above.

Figure 2:
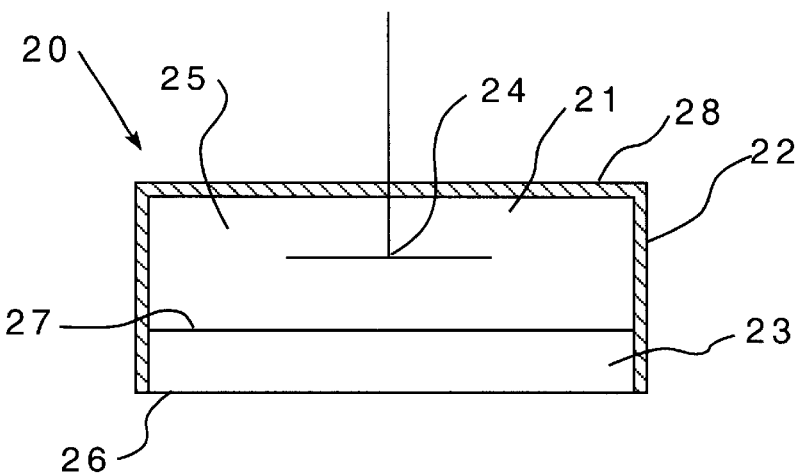
FIG. 2 is a cross-sectional view of a cathode patch of the present invention.

Referring now to FIG. 2, the cathode patch 20 is shown in a sectional view. Similar to the anode patch, the cathode patch 20 includes a two compartment structure. The cathode patch 20 includes an electrode compartment 21 and a skin contacting compartment 23 which can be utilized for cathodic delivery of anionic (negatively charged) drugs to the patient.

The cathode patch 20 is provided with a housing 22 which can be fabricated similarly to the anode patch. The housing 22 includes an electrode compartment which includes the cathodic electrolyte (catholyte) 25 and the metal electrode or cathode 24. In a preferred embodiment, the electrolyte 25 includes the metal ions which are reduced during the electrochemical reaction.

The cathode patch 20 optionally includes a release liner 26 which may be fixed to the underside of the skin contact compartment by an adhesive. The release liner 26 protects the skin contact compartment surface from contamination and damage when the device is not in use. When the device is ready for use, the release liner 26 may be peeled off to expose the skin contact compartment surface for application of the cathode to a patient.

The cathode patch 20 may also include a suitable backing film 28 positioned on top of the electrode compartment 21. The backing film 28 provides protection against contamination and damage to the electrode compartment of the cathode patch of the iontophoretic device.

The cathode 24, as described earlier, has two embodiments as depicted in FIG. 2a and FIG. 2b. In one embodiment of the present invention, the cathode is fabricated from a single material 243 which is both an electrically conductive material (good electron conductor) and a good chemically inert material, including but not limited to platinum, gold, copper, silver and palladium.

Figure 2A:
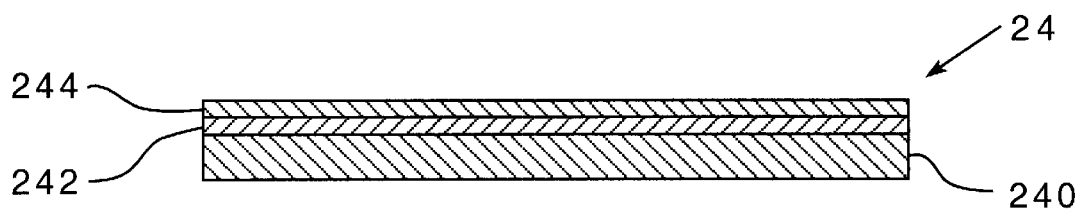
FIG. 2a is an exploded cross-sectional view of the two-layered embodiment of the cathode electrode of the present invention.

In a preferred embodiment as depicted in FIG. 2a the cathode may be formed from a composite of two materials 242, 244. A patch of the cathode being formed of a material which is a good electron conductor but has no or limited chemical inertness 242. By way of example and not limitation, such material may include copper, silver, aluminum, zinc, iron or a variety of known conductive polymers, conductive adhesives or ceramics or the like. This is material is then coated with a chemically inert electron conductor 244. By way of example and not limitation, the coating material may be made of carbon, platinum, gold or any other chemically inert material having good or limited electron conductive ability.

Figure 2B:
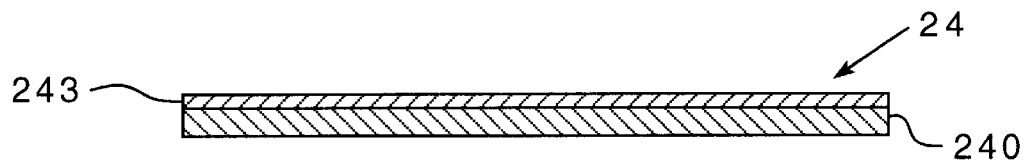
FIG. 2b is an exploded cross-sectional view of the single-layered embodiment of the cathode electrode of the present invention.
Figure 2C:
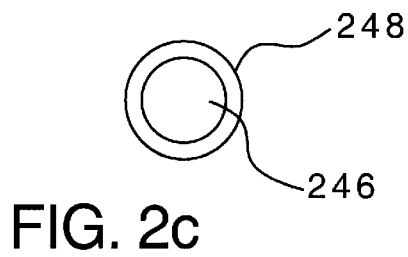
FIG. 2c is an exploded cross-sectional view of a strand of a mesh cathode electrode of the present invention which is comprised of two layers.

In an alternative embodiment, the cathode may be formed similar to the earlier described anode of the preferred embodiment. As depicted in FIG. 2c the cathode of the present invention may be formed from a mesh 246, a material which is a good electron conductor but has no or limited chemical inertness, which is coated with a material 248 which is a chemically inert electron conductor. More specifically, the cathode may be formed from an expanded copper foil mesh 246 which is coated with a chemically inert material, such as carbon or graphite 248. The same reaction, reduction of metal ions to metal would occur at the cathode.

One preferred embodiment of the cathode 24 is illustrated in FIG. 2a and is fabricated on a thin flexible polymeric film 240. The thin polymer film 240 includes a layer of electrically conductive material 242, such as a metallic conductor, i.e., silver or copper, bonded to one side of the film material. The cathode further includes a layer of material which is chemically inert but is a good or limited electron conductor 244, such as carbon or graphite bonded to the electrically conductive material layer 242.

Printed ink technology can be used to form the electrodes of the present invention, as described in U.S. Ser. No. 08/012,168 now abandoned, filed Feb. 2, 1993 the disclosure of which is herein incorporated by reference. Separate inks containing each of the desired materials would be formulated and separately applied. The ink may be applied to the polymeric film by techniques which include, but are not limited to, impression, lithography, offset, gravure, jet application, silk-screening and the like. Alternatively, if the conductive material 242 is a metal or metallic material, it may be applied to the polymeric film by electroplating, vacuum sputtering or any other method so that a uniform metallic layer is formed. Using printed ink technology a manufacturer may selectively pattern the shape and size of the electrodes and thus reduce cost and increase the ease of manufacturing.

As discussed above, and illustrated in FIG. 2b another preferred embodiment provides that the cathode may be fabricated from a single layer of material 243 which is both chemically inert electron conductor and an electrically conductive material (examples of which were provided above). The single layer of material may also be applied to a polymeric film 240 by techniques described above.

The multiple layer construction of the cathode formed on a polymeric film backing promotes excellent conductivity in both the horizontal and vertical axes of the cathode. The present invention produces a cathode electrode which is formulated from highly chemically inert as well as a good electron conductor in both the horizontal and vertical axes, this is accomplished by combining material with high electron conductivity and low or no chemical inertness with materials that are chemically inert but have limited or good electron conductivity, such as for example carbon coated with silver. More specifically, carbon is a highly polarized conductor, i.e., carbon conducts well in one direction only. The thin coating of carbon applied to the cathode of the present invention is conductively polarized so that excellent conductivity exists along the vertical axis of the cathode as shown in FIGS. 2a and 2b.

Thus, by utilizing a metallic layer of silver, copper, aluminum, etc. in the cathode, all of which have excellent conductivity in the horizontal direction along the film, conductivity in both the horizontal and vertical axis is achieved. The metallic layer conducts in the direction of both axis, thus enhancing the conductivity of carbon along the horizontal axis. This kind of structure guarantees uniform current collection and distribution. A cathode constructed in this manner is highly effective, yet achieves the cost savings and manufacturing ease which are objects of the present invention. In addition, chemical inertness of the carbon layer protects the metallic layer from degradation during storage and use. This is especially important when using base metals such as copper or aluminum, which tend to degrade during storage.

In an alternative embodiment, for short-term usage, the cathode may be fabricated from silver-coated copper. Preferably, the copper is in the form of a expanded foil mesh and the silver coating is provided to prolong shelf-life by inhibiting the copper cathode from reacting with the electrolyte when the device is not in use. The operation of the cathode is similar to that of the carbon/silver film cathode. Specifically, copper ions formed in electrolyte are plated on to the cathode.

Referring back to FIG. 2, the cathode patch 20 preferably includes an ion regulating means 27 between the cathode compartment 21 and the skin contacting compartment 23. The ion regulating means described above, is used to prevent the copper cations in the electrolyte chamber from reaching the skin contacting compartment. Additionally, the ion regulating means prevents the metal ions present in the electrolyte from transporting away from the cathode electrode and from participating in the electrochemical reaction $M^{n+}+ne^- \rightarrow M$ which takes place at the cathode electrode. To ensure the availability of the metallic cation for the electrochemical reaction it is preferred that the ion regulating means be in the form of an anionic membrane or anionic beads which act as a barrier to keep the metallic cations from transporting into the skin contacting compartment by repelling them and keeping the metallic cations in the electrode compartment.

Another consideration when designing an electrode system for an iontophoretic device is the over voltage of the electrode pair. Over voltage is defined as the deviation from the thermodynamic equilibrium potential. More specifically, over voltage is the extra voltage one would have to supply to maintain the electrode reaction at a certain rate. With respect to iontophoretic devices, a good electrode system has a low over voltage, typically <100 mV at the current densities of interest to iontophoresis. Additionally, a good electrode exhibits stability in its voltage characteristics. Stability is defined as a basically flat voltage curve over the entire period of utilization.

In the preferred electrode system of the present invention, a substantially copper or aluminum anode and a carbon/silver cathode with copper/zinc salt catholyte exhibit both good over voltage characteristics and voltage stability (as presented in the examples below). Additionally, since the preferred electrode systems do not provide sufficient voltage to the electrolyte to achieve electrolysis of water, no H+ or OH− ions are generated. Accordingly, no pH change occurs. It is important not to alter pH so that the patient will not experience discomfort from pH burns to the skin.

As discussed above, iontophoretic devices require at least two electrodes, an anode and a cathode, to provide a potential to drive drug ions into the skin of a patient. Both electrodes are disposed to be in intimate electrical contact with the skin thereby completing the electrochemical circuit formed by the anode and cathode of the iontophoretic device. The electrodes may be further defined as an active electrode from which an ionic drug is delivered into the body and an indifferent or ground electrode which serves to complete the electrochemical circuit. In some cases, depending upon the electrode materials, a battery or other current source is coupled to the electrodes to provide the electrical force (power source) to drive the drug ions into the body.

The ionic drug can be delivered from either the anode, the cathode, or both simultaneously or alternatively. For example, if the ionic substance to be driven into the body is positively charged, then the positive electrode or anode will be the active electrode and the negative electrode or cathode will serve as the indifferent or ground electrode to complete the electrochemical circuit. Alternatively, if the ionic substance to be delivered is negatively charged, then the negative electrode will be the active electrode and the positive electrode will be the indifferent or ground electrode.

In an especially preferred embodiment, the anode and cathode form a galvanic couple to which produces sufficient current to drive the electrode reaction.

Additionally, even if this galvanic couple does not provide sufficient potential difference to drive the electrode reaction, it will reduce the energy requirements of the iontophoretic device.

In another preferred embodiment, a galvanic couple is not formed, by the anode patch and the cathode patch, thus the device will require an external power source to drive or assist in driving the electrode reaction. The positive terminal of the external power source is coupled to the anode patch of the device and the negative terminal of the external power source is coupled to the cathode patch of the device.

Whether or not a galvanic couple is formed, it is most preferable that the anode is formed from substantially copper or aluminum and the cathodic electrochemical reaction is the reduction of copper or zinc from an electrolyte containing the corresponding salt. The preferred catholyte 36 is chloride or sulfate salts of copper or zinc in a gel matrix. In the preferred embodiment, when voltage is applied to the device, the copper ions formed in the electrolyte solution plate on to the cathode 34. The corresponding electrochemical reaction is as follows:

$$Cu^{+2} + 2e^- \to Cu$$

The copper ions, $Cu^{+2}$, are supplied by the electrolyte in the cathode. Although cupric chloride is the preferred cathodic electrolyte salt, any biocompatible soluble metal salt may be used. Suitable metal salts include but are not limited to copper sulfate, zinc chloride, zinc sulfate and other zinc and copper salts.

The following examples are presented by way of illustration and not limitation.

EXAMPLE 1

In-Vitro 24 Hour Patch Testing

The following example provides a general description of how each of the in vitro examples were run using various embodiments of the present invention. Each example, 2 through 7 will provide information specifically directed to the type of anode, cathode, electrolyte, ion regulating mean or compartment separator used therein.

As indicated below this (in vitro) Example 1 was run using a traditional silver anode, silver chloride cathode and sodium chloride catholyte. The objective of this example is to determine the electrode/patch performance of different electrochemical configurations by monitoring potentials, pH effects, electrochemical deposition and ion transport. The experimental setup for this example was as follows:

Materials

Anode Compartment Separation Means: YCO5 size exclusion membrane
Cathode Compartment Separation Means: AXM-7001 anion exchange membrane
IRP69 cation exchange resin
Seakem Gold Agarose
Faisson Foam (⅛", 1/16", 1/32")
BDTS Ag/AgCl wire reference
Saline
Excised Pig Skin
Electrode Material:
    Anode (6 Ag 1077 Delker Mesh)
    Cathode chlorided 6 Ag 1077 Delker Mesh
Electrolyte
Anode skin compartment 3 wt % Agarose+10 mM NaCl
Cathode skin compartment 3 wt % Agarose+150 mM NaCl

Equipment

Power Supply
Keithly Data Bucket
Patch Test Stand
250 ml, 500 ml Beaker
Microwave
2 sq. cm agarose plug mold
Micrometer

Patch Preparation

The Faisson Foam is cut into donut rings with the desired inner area and thickness. Next, the electrodes are cut to the desired area using a roll press. Cut out the anode separator and the cathode separator to the desired area. The patches are then constructed using the foam rings, the separators, the BDTS wire references and the electrodes so that the patch meets the desired specifications. FIG. 1 shows a typical patch configuration for an Ag anode patch and FIG. 2 shows a typical configuration for a AgCl cathode patch. Make sure that the foam rings are well sealed around the various electrode parts.

Solution Preparation

To prepare the electrolyte, make a mixture of the desired amount of Agarose with the electrolyte of interest (see below for examples). The mixture is heated until the Agarose is in solution. This is usually indicated by a color change from murky to clear. In the cases where IRP69 is in solution, heat until the solution is boiling.

Examples of common electrolyte solutions:

Anolyte: 3 wt % Agarose/25 wt % IRP69/10 mM NaCl

Catholyte: 3 wt % Agarose+150 mM NaCl

Loading Electrolyte Into Patch

The prepared electrolyte is loaded into the appropriate patch compartment and allowed to cool. Seal the anode and cathode compartment by placing a 3M acrylic adhesive film over the top. This will reduce $H_2O$ loss due to evaporation in the patch.

Preparing the Test Stand

Figure 3:
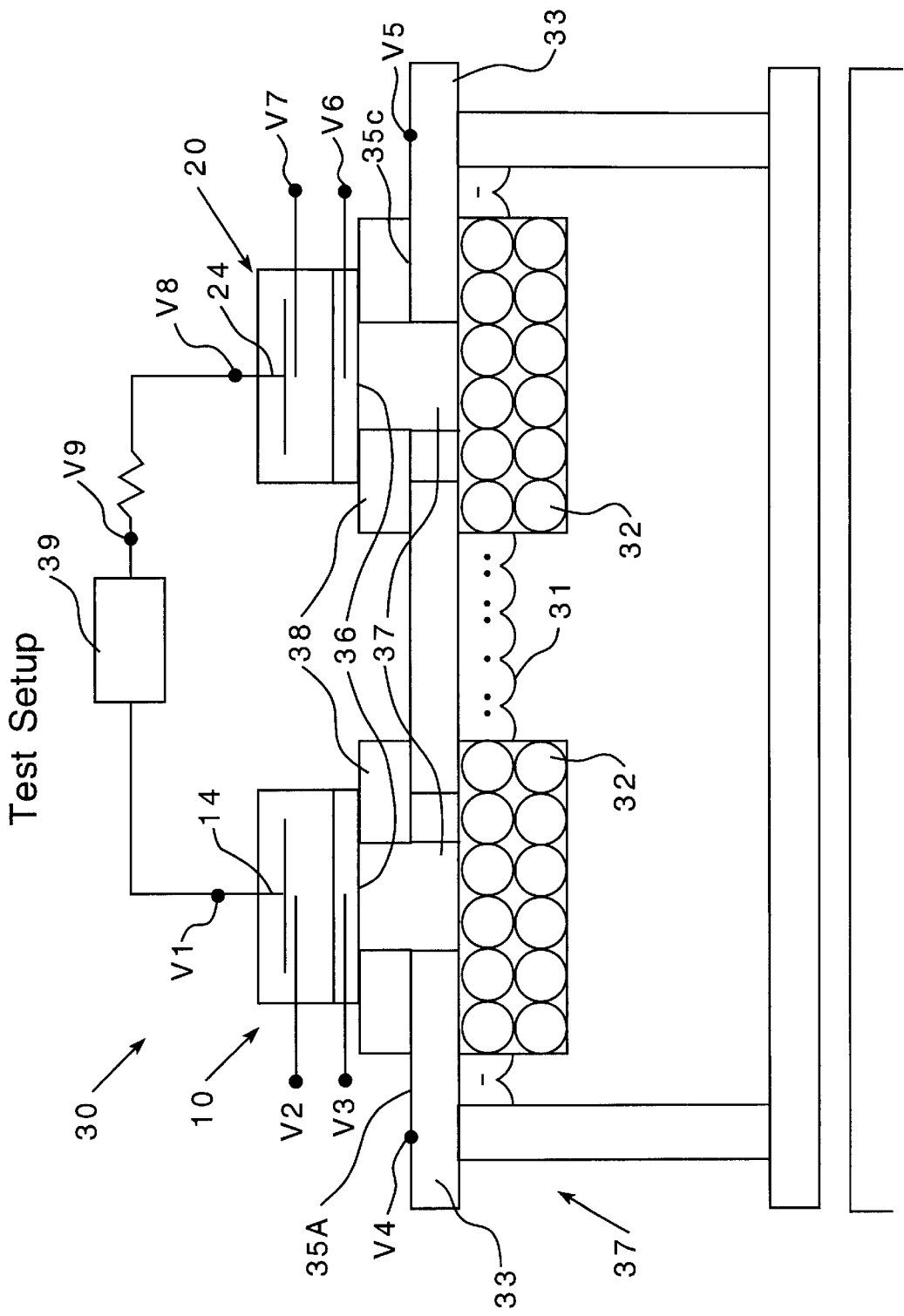
FIG. 3 depicts the test stand for in vitro 24-hour patch test.

FIG. 3 shows the prepared test stand. The test stand is prepared by filling the test stand 30 with 0.9 wt % saline 31 until the liquid level covers half of the porex discs 32 located underneath the top plate 33 of the test stand. Screw the top plate 33 into place. Place the agarose plug 34 onto the porex and place a BDTS reference wire 35a (anode-side), 35b (cathode-side) into the plug. Next, place a piece of excised pig skin 36 over the agarose plug 34 and place the cover plates 38 over the plug. Screw the cover plates 38 into place, being careful to make sure that the skin 36 is approximately level with the top of the cover plate 38.

Starting the Experiment

Place an anode patch 10, as depicted in FIG. 1, and a cathode patch 20, as depicted in FIG. 2, on the test stand 37 of FIG. 3. Insure that the cover plates 38 are dry before patch placement to avoid the patches 10 and 20 from coming off during the run. Connect the positive lead of the power supply to the anode 14 and the negative lead to the cathode 24. Next connect the monitoring device (not shown in Fig.) to the patch to measure electrode potentials (anode V1–V2, cathode V7–V8); separator voltages (anode V2–V3, cathode V6–V7); skin voltages (anode V3–V4, cathode V5–V6); cell voltage (V4–V5); total voltage (V1–V8) and current (via 100 ohm resistor (V8–V9)). Next, set the current on the power supply to the desired level. Turn on the monitoring device to get the time=0-reading. Turn on the power supply 39 and allow the current to run for 24 hours.

Ending the Experiment

At the end of 24 hours, turn off the power supply 90. Once the power supply is off, remove the monitoring device from the patches. Remove the patches from the stand and separate the different compartments of the patch. Measure the pH changes in the patch. Extract the gels and measure the electrolyte salt concentrations, in this case $Na^+$ and $Cl^-$ concentrations.

Data Analysis

Figure 4:
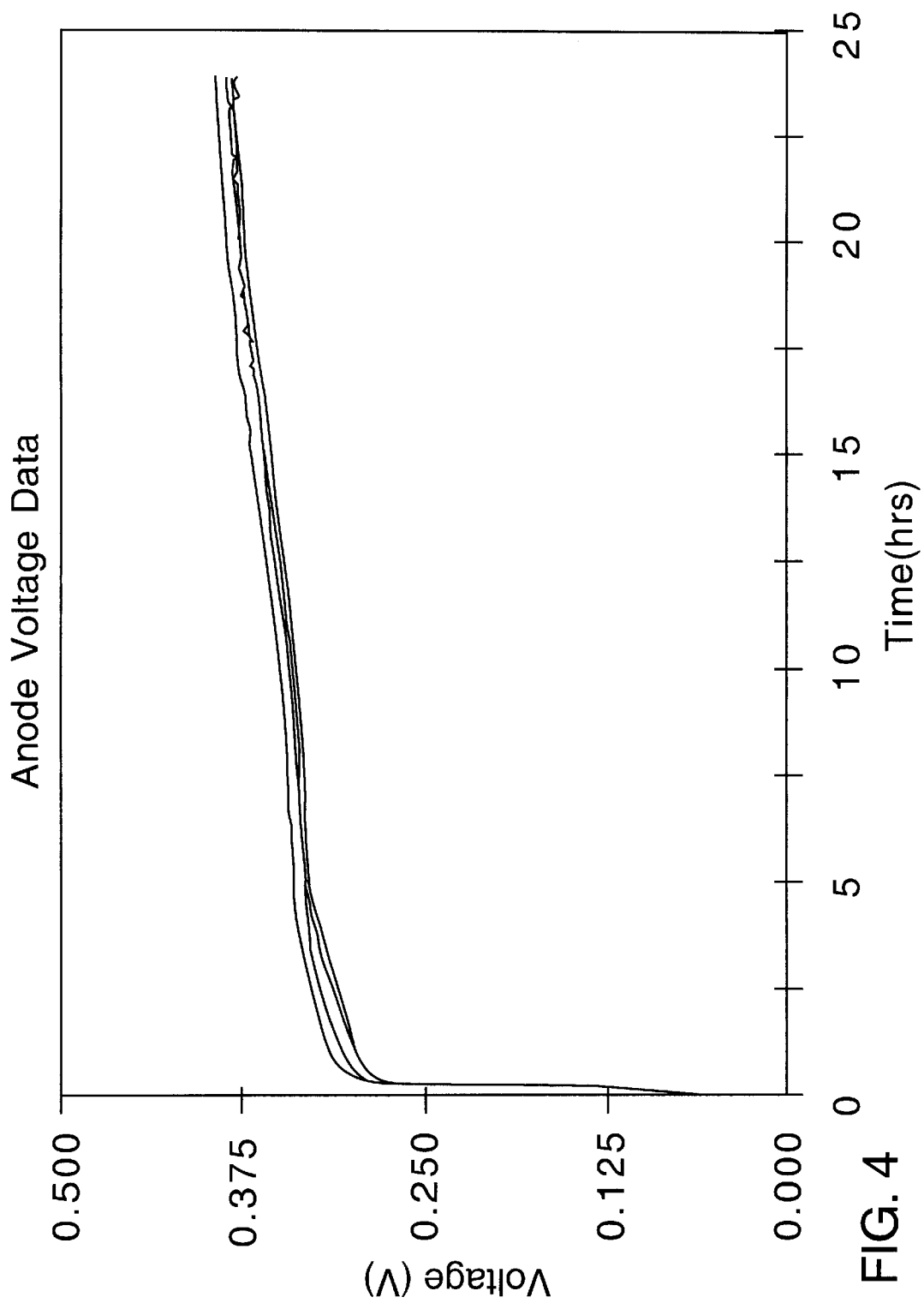
FIG. 4 is a graph illustrating in vitro performance data of a silver anode.
Figure 5:
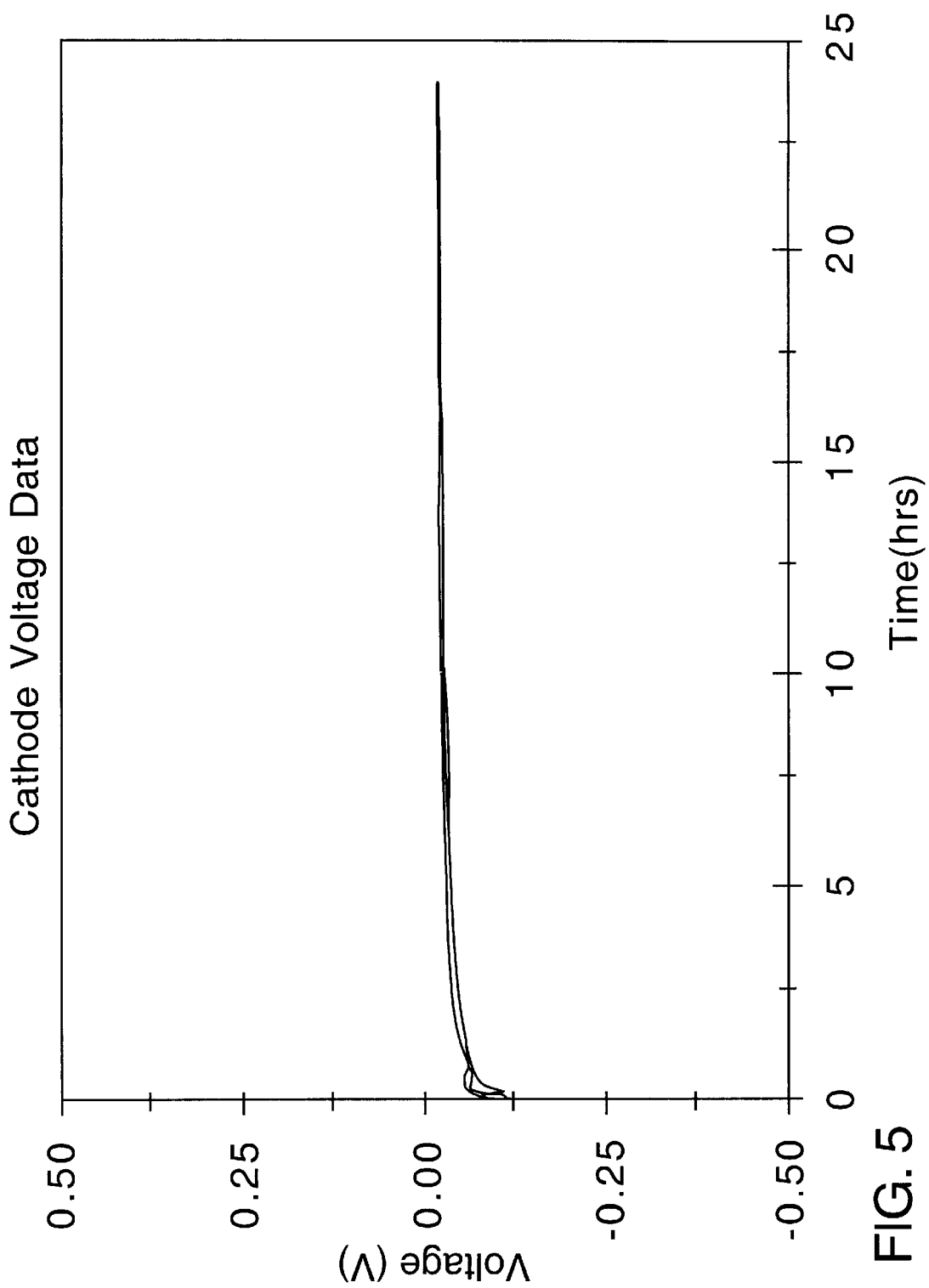
FIG. 5 is a graph illustrating in vitro performance data of a silver chloride cathode

FIGS. 4 and 5 illustrate electrode performance data in patch configuration obtained with the traditional Ag anode FIG. 4 and AgCl cathode FIG. 5 on the standard in vitro test platform using excised porcine skin. Details of the patch and the test conditions have been described above. The anode was formed from a silver Delker mesh (6 Ag 10077) and the cathode was formed from a silver Delker mesh coated with silver chloride (chlorided 6Ag 10077). Additionally, the cathode electrolyte comprised 150 mM NaCl saline plus 3 wt. % agarose. The test was run for a period of 24 hrs and at a current density of 0.4 mA/cm$^2$. Four (N=4) repeat experiments were run to determine reproducibility.

The data suggests good reproducibility with the four runs. In general the polarizations were found to be stable, low, and reproducible suggesting good electrode performance over the 24 hr. period. The primary anode electrochemical reaction is the dissolution of silver to silver ions and the primary cathode reaction is the reduction of silver chloride to silver.

EXAMPLE 2

The objective of the following example is to determine the in vitro electrode/patch performance of a silver coated copper anode of the present invention. The experimental test set-up for this example is the as the experimental test set-up for Example 1.

Figure 6:
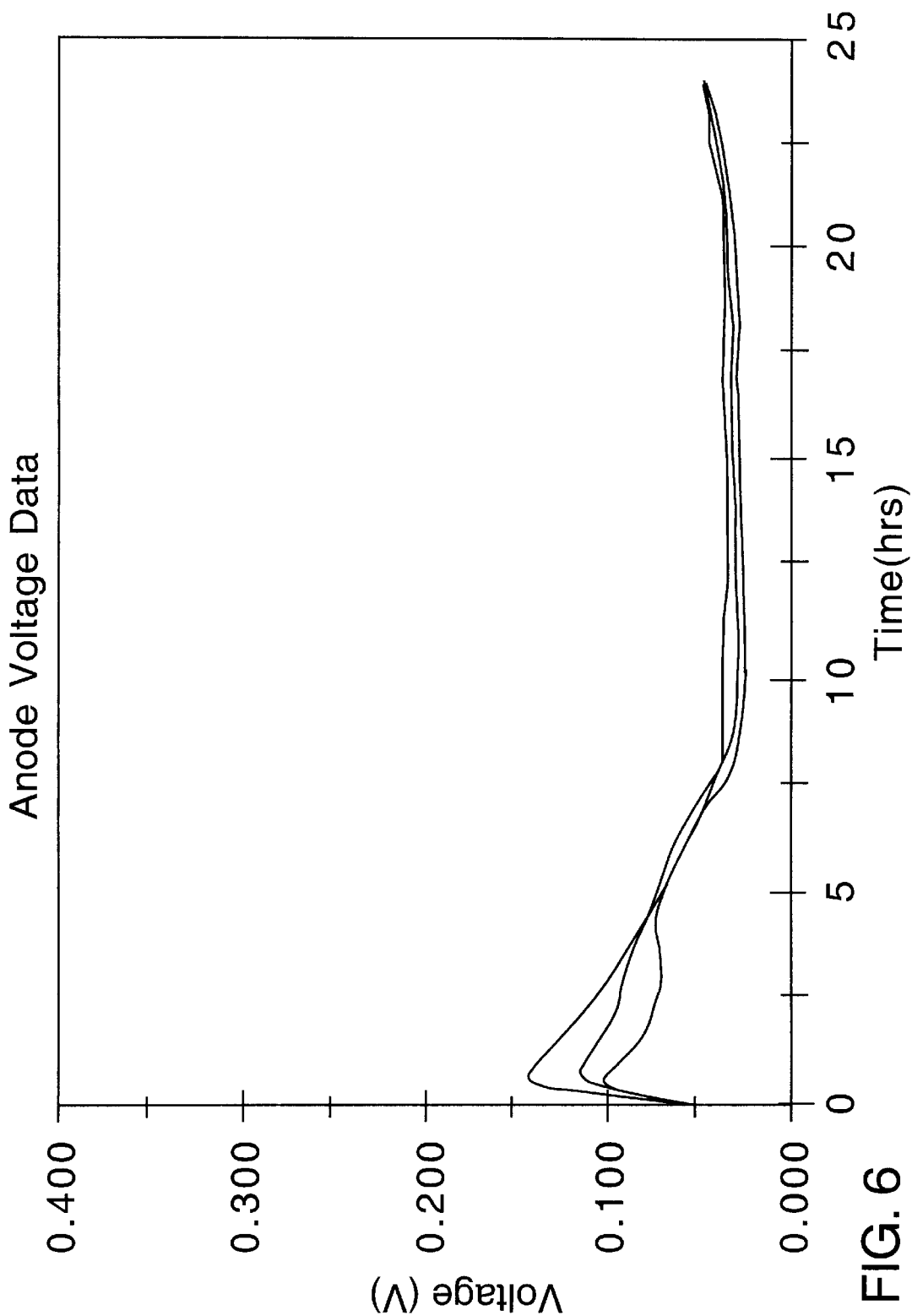
FIG. 6 is a graph illustrating in vitro performance data of a silver-coated copper anode of the present invention.

FIG. 6 presents anode performance data in patch configuration obtained with silver coated copper (Ag/Cu) anodes on the standard in-vitro test platform using excised porcine skin. The anode patch configuration is as follows: 3 wt % Agarose +25 wt % IRP69+10 mM NaCl (1/32")/"0.1 mil" Ag Coated 4Cu 7-100 Delker Mesh/3 wt % Agarose+25 wt % IRP69+10 mM NaCl (1/4")/Y-CO5 Size Exclusion Membrane/3 wt % Agarose+10 mM NaCl (1/8"). The exposed electrode area was 2 cm$^2$ and the operating current density was 0.2 mA/cm$^2$. The test was run for 24 hours at room temperature. The single electrode potential data was monitored with a Ag/AgCl wire reference electrode and recorded using a Fluke data logger. Unless otherwise stated all the voltage data described will be versus Ag/AgCl as the reference. Three (N=3) repeat experiments were run to determine reproducibility.

The data suggests good reproducibility with the three runs. In general the anode potential rises to a maximum (100–150 mV) within the first hour and then gradually decreases to a steady state value of ~40 mV in 5–6 hours and then remains relatively constant for the remainder of the test period (15–16 hours). It must be noted that the anode polarization is stable, low and reproducible suggesting good electrode performance over the 24 hour test period.

The rise and fall of the electrode potential in the initial period is attributed to the switch in the anode reaction from Ag electrochemistry to Cu electrochemistry. When the current is first turned on, the Ag surface in contact with 10 mM NaCl is oxidized to AgCl as per equation 6–1 and the polarization is low.

$$Ag + Cl^- \longrightarrow AgCl + e^- \qquad (6\text{-}1)$$

But since the Cl— ion concentration is low, the electrode surface quickly gets depleted of Cl— ion to support equation 1 and the electrode reaction then transitions to Ag dissolution at a higher potential as given by:

$$Ag \rightarrow Ag^+ + e- \quad (6\text{-}2)$$

This explains the rising portion of the anode potential in the initial period. As the Ag coating is electrochemically dissolved off the electrode copper gets exposed and the copper dissolution reaction begins (see equation 3) forcing the electrode potential trace to decrease and finally reach steady state dominated by copper dissolution reaction in 5–6 hours.

$$Cu \rightarrow Cu^{2+} + 2e- \quad (6\text{-}3)$$

At the end of the experiment, the porcine skin under the anode compartment was analyzed for copper concentration using atomic absorption spectroscopy. For baseline purposes, a sample of fresh unused porcine skin was also simultaneously analyzed. The results of the copper ion concentrations in the anode porcine skin are presented in Table 6-1. As seen from Table 6-1 the copper ion concentration in the anode porcine skin was less than 5 ppm (below the detection limits of the AA analyzer) demonstrating effective regulation of the transport of the electrochemically generated copper ions at the anode from reaching the skin by the cation exchange beads. pH measurements were also done at the end of the experiment on the electrode surface and on the gel surfaces in the electrode compartment. No detrimental pH effects were observed and the pH was measured to be 6.

TABLE 6-1

Copper ion concentration data in in-vitro skin with Ag/Cu anode.

| | Concentration (ppm) |
|---|---|
| Fresh unused skin | <5 |
| Anode skin 1 | <5 |
| Anode skin 2 | <5 |
| Anode skin 3 | <5 |

EXAMPLE 3

The objective of the following example is to determine the in vitro electrode/patch performance of an aluminum anode of the present invention. The experimental test set-up for this example is the as the experimental test set-up for Example 1.

Figure 7:
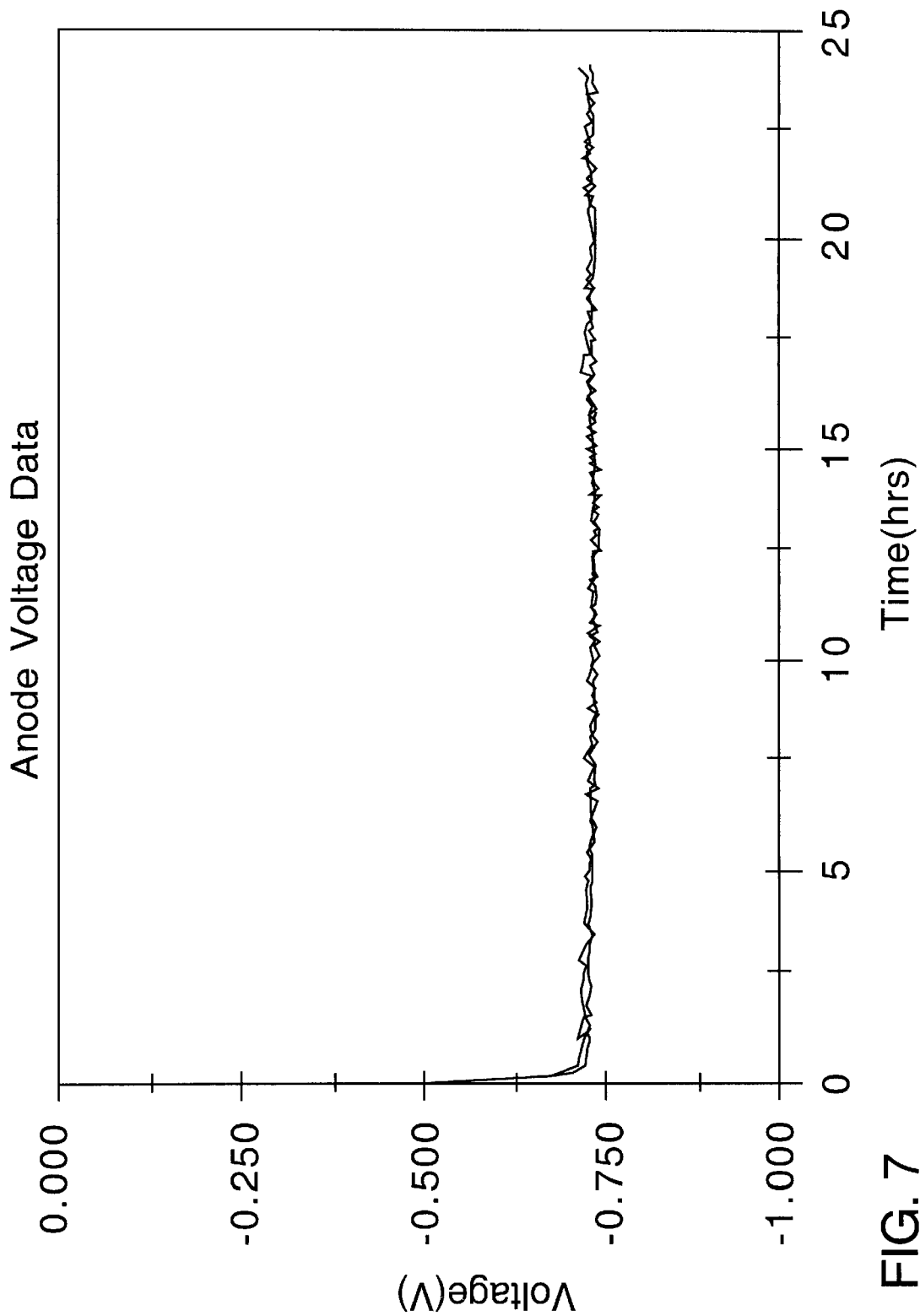
FIG. 7 is a graph illustrating in vitro performance data an aluminum anode of the present invention.

FIG. 7 presents anode performance data in patch configuration obtained with Aluminum anodes on the standard in-vitro test platform using excised porcine skin. The anode patch configuration is as follows: 3 wt % Agarose+25 wt % IRP69+10 mM NaCl (1/32")/4A18-100 Delker Mesh/3 wt % Agarose+25 wt % IRP69+10 mM NaCl (1/4")/YCO5 Size Exclusion Membrane/3 wt % Agarose+10 mM NaCl (1/8"). The exposed electrode area was 2 cm² and the operating current density was 0.2 mA/cm². The test was run for 24 hours at room temperature. The single electrode potential data was monitored with a Ag/AgCl wire reference electrode and recorded using a Fluke data logger. Unless otherwise stated all the voltage data described will be versus Ag/AgCl as the reference. Four (N=4) repeat experiments were run to determine reproducibility.

The data suggests excellent reproducibility with the four runs. The anode potential is relatively stable and flat at ~−0.74V over the entire 24 hours of test suggesting stable reproducible performance. The primary electrochemical reaction at the anode is oxidation of Al to $Al^{3+}$ as given by:

$$Al \rightarrow Al^{3+} + 3e- \quad (7\text{-}1)$$

But electrode potential measured is more positive than its normal equilibrium potential suggesting high polarizations at the electrode. However the majority of this shift in potential is caused by the passivation phenomenon of aluminum in aqueous saline solutions causing the normal equilibrium potential to shift at least 1V more positive. Therefore we can conclude that the polarizations at the aluminum electrode are actually low suggesting good electrode performance.

At the end of the experiment, the porcine skin under the anode compartment was analyzed for aluminum concentration using atomic absorption spectroscopy. For baseline purposes, a sample of fresh unused porcine skin was also simultaneously analyzed. The results of the aluminum ion concentrations in the anode porcine skin are presented in Table 7-1. As seen from Table 7-1 the copper ion concentration in the anode porcine skin was less than 5 ppm (below the detection limits of the AA analyzer) demonstrating effective regulation of the transport of the electrochemically generated copper ions at the anode from reaching the skin by the cation exchange beads.

pH measurements were also done at the end of the experiment on the electrode surface and on the gel surfaces in the electrode compartment. No detrimental pH effects were observed and the pH was measured to be 6.

TABLE 7-1

Aluminum ion concentration data in in-vitro skin with aluminum anode.

| | Concentration (ppm) |
|---|---|
| Fresh unused skin | <5 |
| Anode skin 1 | <5 |
| Anode skin 2 | <5 |
| Anode skin 3 | <5 |
| Anode skin 4 | <5 |

Lower Patch Voltage

The following conclusions are based on the thermodynamics and voltage balance relationships as a result of comparing Examples 1 through 3. From thermodynamics and voltage balance relationships it can be shown that the patch voltage required to operate an iontophoretic patch will decrease as the anode potential decreases and the cathode potential increases. Comparing data from FIG. 7 with FIG. 6 and FIG. 4, it is obvious that an Aluminum anode will operate at a potential ~1V more negative compared to a Ag/Cu anode or Ag anode. Hence use of Aluminum as the anode material will result in reducing the operating patch voltage by at least 1V compared to a Ag or Ag/Cu anode patch.

EXAMPLE 4

The objective of the following example is to determine the in vitro electrode/patch performance of a carbon coated silver cathode using a $ZnCl_2$ electrolyte of the present invention. The experimental test set-up for this example is the as the experimental test set-up for Example 1.

Figure 8:
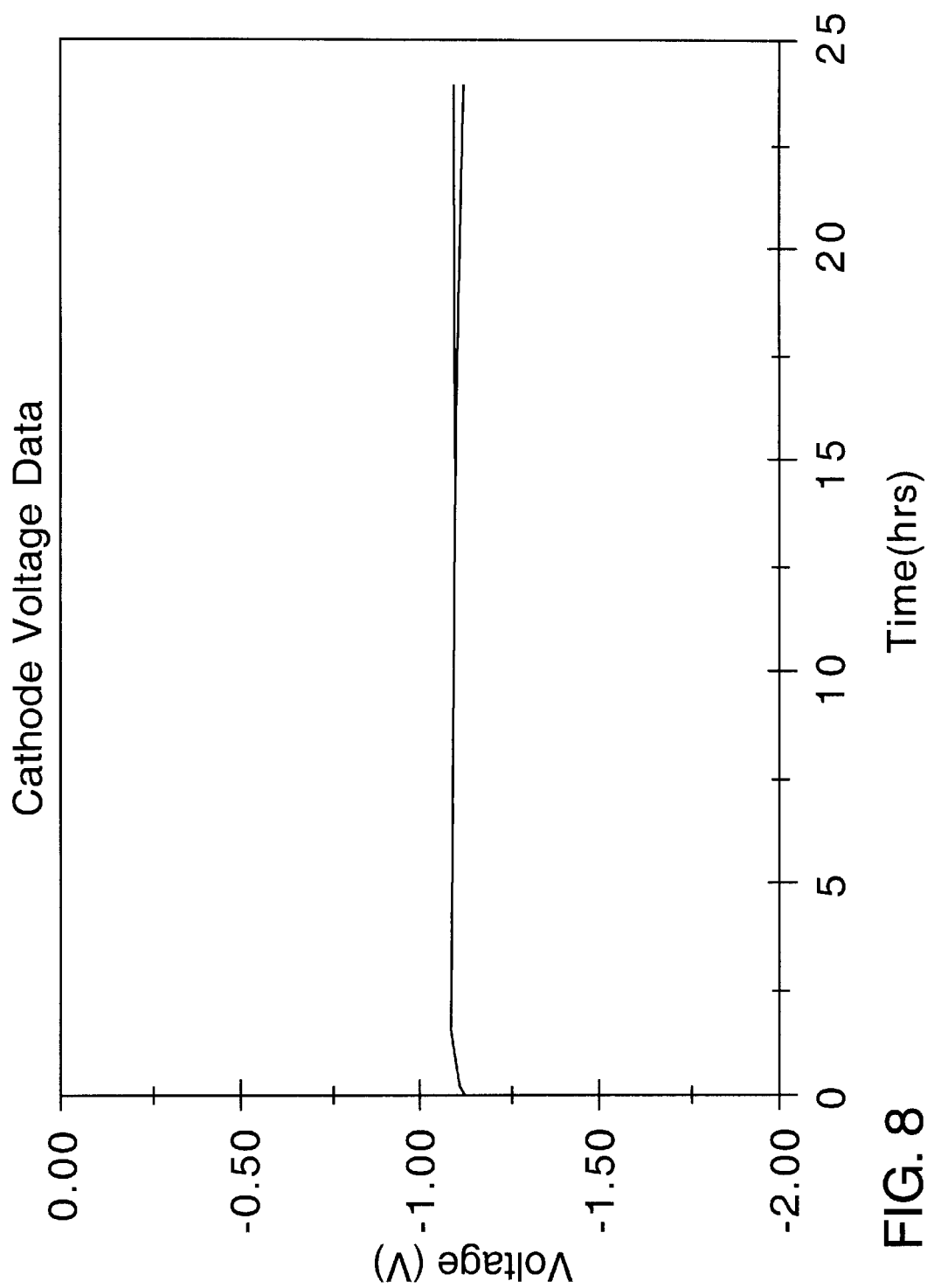
FIG. 8. is a graph illustrating in vitro performance data of a carbon coated silver cathode in an electrolyte containing $ZnCl_2$.

FIG. 8 presents cathode performance data in patch configuration obtained with carbon coated silver cathode and zinc chloride electrolyte on the standard in-vitro test platform using excised porcine skin. The cathode patch configuration is as follows: 3 wt % Agarose+150 mM $ZnCl_2$ (⅛")/C/Ag Printed Ink/3 wt % Agarose+150 mM $ZnCl_2$ (¼")/Anion Exchange Membrane, ESC-7001/3 wt % Agarose+150 mM NaCl (⅛"). The exposed electrode area was 2 $cm^2$ and the operating current density was 0.2 $mA/cm^2$. The test was run for 24 hours at room temperature. The single electrode potential data was monitored with a Ag/AgCl wire reference electrode and recorded using a Fluke data logger. Unless otherwise stated all the voltage data described will be versus Ag/AgCl as the reference. Three (N=3) repeat experiments were run to determine reproducibility.

The data suggests good reproducibility with the three runs. The cathode potential is relatively stable and flat at ~−1.1V over the entire 24 hours suggesting stable reproducible performance. The primary electrochemical reaction at the cathode is the reduction of $Zn^{2+}$ to Zn as given by:

$$Zn^{2+} + 2e- \rightarrow Zn \qquad (8\text{-}1)$$

The polarization at the cathode is very low (<100 mV) suggesting good electrode performance.

At the end of the experiment, the porcine skin under the cathode compartment was analyzed for zinc concentration using atomic absorption spectroscopy. For baseline purposes, a sample of fresh unused porcine skin was also simultaneously analyzed. The results of the zinc ion concentrations in the cathode porcine skin are presented in Table 8-1. As seen from Table 8-1 the zinc ion concentration in the fresh unused skin was 14 ppm and in the cathode skin was 27 ppm demonstrating the anion exchange membrane blocking substantial transport of the zinc cations from the cathode compartment to the skin.

pH measurements were also done at the end of the experiment on the electrode surface and on the gel surfaces in the electrode compartment. No detrimental pH effects were observed and the pH was measured to be 5.

TABLE 8-1

Zinc ion concentration data in in-vitro skin with C/Ag printed ink cathode & Zinc chloride electrolyte.

| | Concentration (ppm) |
|---|---|
| Fresh unused skin | 14 |
| Cathode skin 1 | 30 |
| Cathode skin 2 | 24 |
| Cathode skin 3 | 28 |

EXAMPLE 5

The objective of the following example is to determine the in vitro electrode/patch performance of a carbon coated silver cathode using a $ZnSO_4$ electrolyte of the present invention. The experimental test set-up for this example is the as the experimental test set-up for Example 1.

Figure 9:
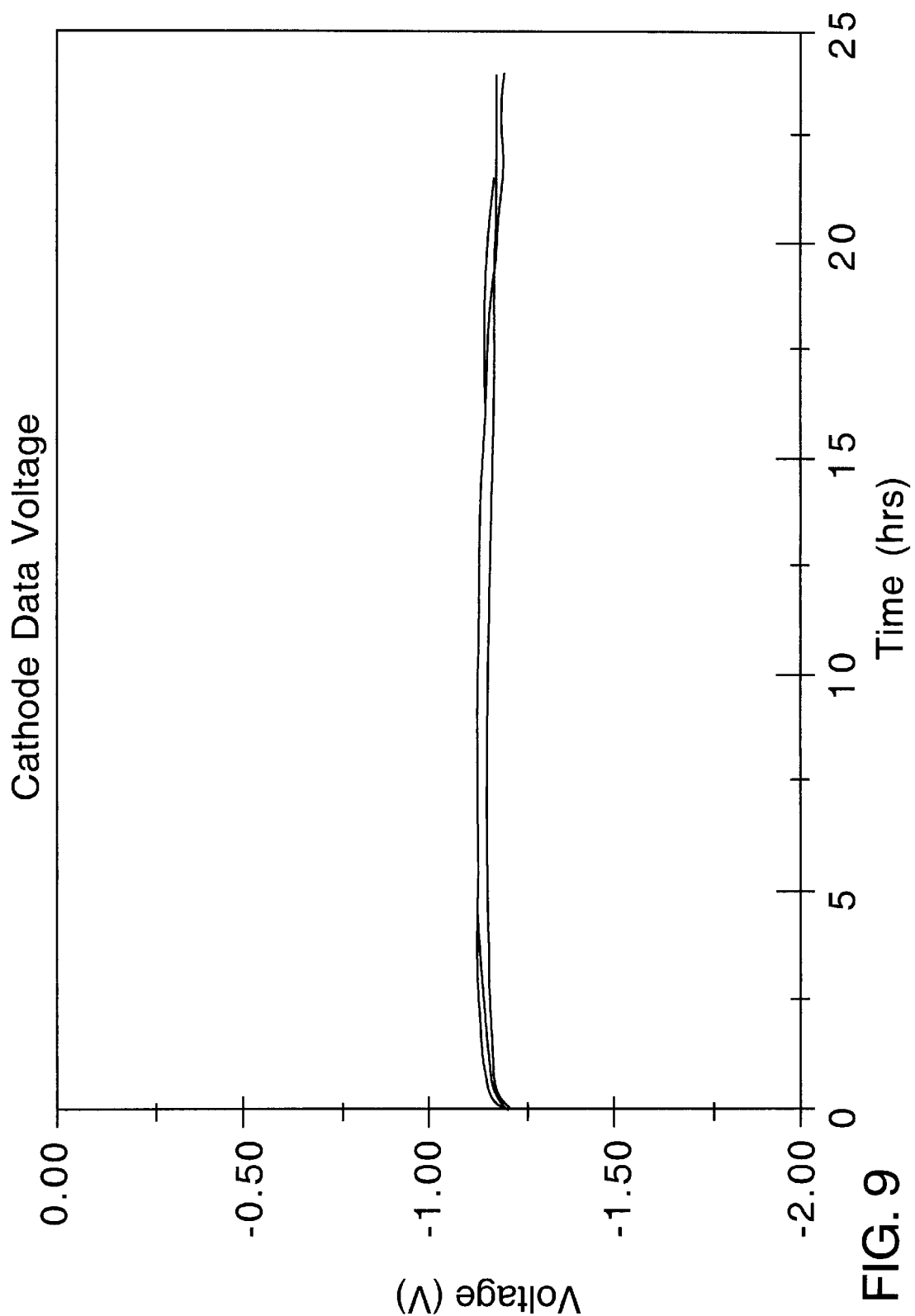
FIG. 9. is a graph illustrating in vitro performance data of a carbon coated silver cathode in an electrolyte containing $ZnSO_4$.

FIG. 9 presents cathode performance data in patch configuration obtained with carbon coated silver cathode and zinc sulfate electrolyte on the standard in-vitro test platform using excised porcine skin. The cathode patch configuration is as follows: 3 wt % Agarose+150 mM $ZnSO_4$ (⅛")/C/Ag Printed Ink/3 wt % Agarose+150 mM $ZnSO_4$ (¼")/Anion Exchange Membrane, ESC-7001/3 wt % Agarose+150 mM NaCl (⅛"). The exposed electrode area was 2 $cm^2$ and the operating current density was 0.2 $mA/cm^2$. The test was run for 24 hours at room temperature. The single electrode potential data was monitored with a Ag/AgCl wire reference electrode and recorded using a Fluke data logger. Unless otherwise stated all the voltage data described will be versus Ag/AgCl as the reference. Four (N=4) repeat experiments were run to determine reproducibility.

The data suggests good reproducibility with the four runs. The cathode potential is relatively stable and flat at ~−1.2V over the entire 24 hours suggesting stable reproducible performance. The primary electrochemical reaction at the cathode is the reduction of $Zn^{2+}$ to Zn as given by:

$$Zn^{2+} + 2e- \rightarrow Zn \qquad (9\text{-}1)$$

The polarization at the cathode is low suggesting good electrode performance.

At the end of the experiment, the porcine skin under the cathode compartment was analyzed for zinc concentration using atomic absorption spectroscopy. For baseline purposes, a sample of fresh unused porcine skin was also simultaneously analyzed. The results of the zinc ion concentrations in the cathode porcine skin are presented in Table 9-1. As seen from Table 9-1 the zinc ion concentration in the fresh unused skin was 17 ppm and in the cathode skin was 41 ppm demonstrating the anion exchange membrane blocking substantial transport of the zinc cations from the cathode compartment to the skin.

pH measurements were also done at the end of the experiment on the electrode surface and on the gel surfaces in the electrode compartment. No detrimental pH effects were observed and the pH was measured to be 5.

TABLE 9-1

Zinc ion concentration data in in-vitro skin with C/Ag printed ink cathode & zinc sulfate electrolyte.

| | Concentration (ppm) |
|---|---|
| Fresh unused skin | 17 |
| Cathode skin 1 | 37 |
| Cathode skin 2 | 38 |
| Cathode skin 3 | 46 |
| Cathode skin 4 | 41 |

EXAMPLE 6

The objective of the following example is to determine the in vitro electrode/patch performance of a carbon coated silver cathode using a $CuCl_2$ electrolyte of the present invention. The experimental test set-up for this example is the as the experimental test set-up for Example 1

Figure 10:
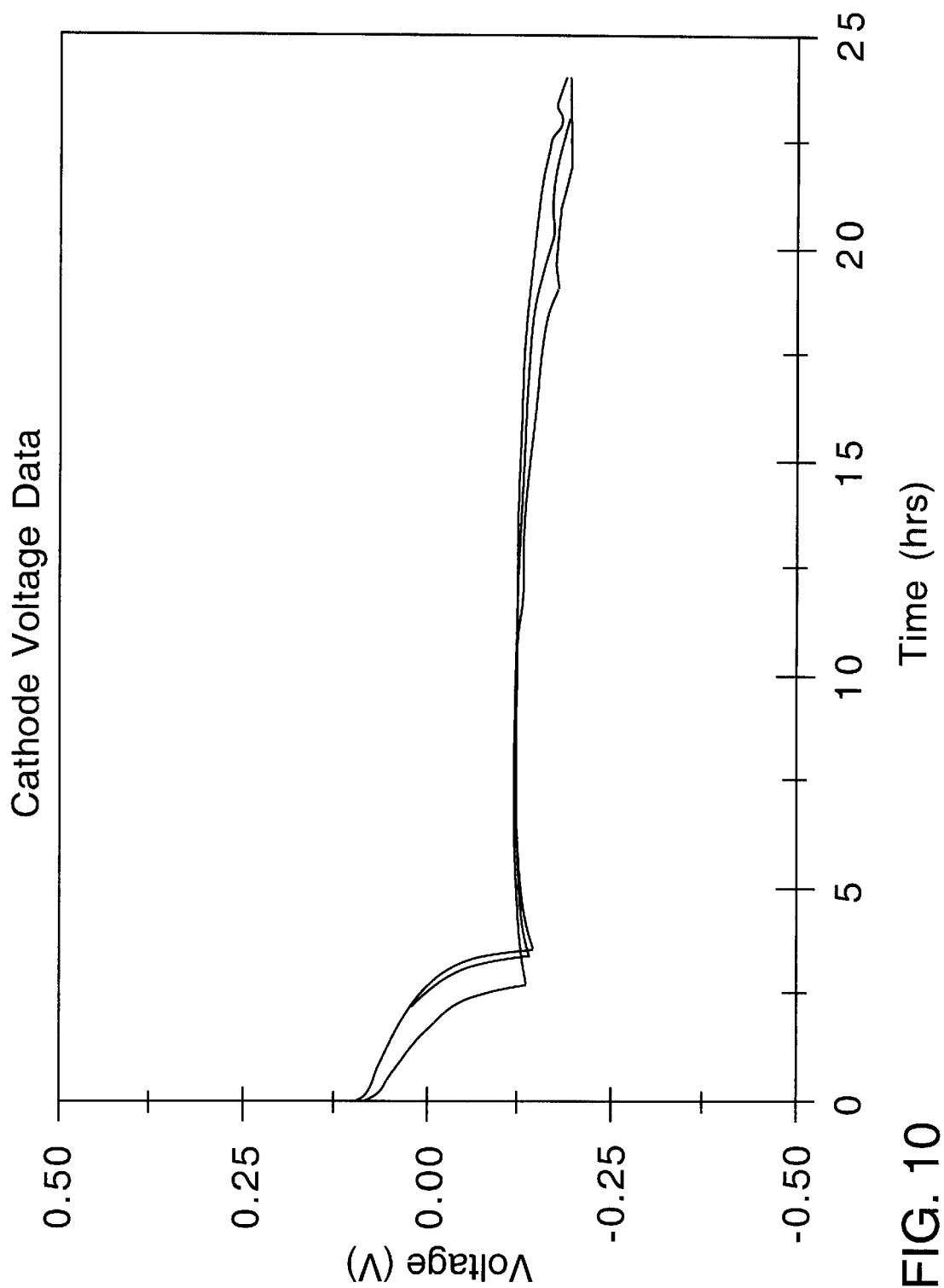
FIG. 10. is a graph illustrating in vitro performance data of a carbon coated silver cathode in an electrolyte containing $CuCl_2$.

FIG. 10 presents cathode performance data in patch configuration obtained with carbon coated silver cathode and copper chloride electrolyte on the standard in-vitro test platform using excised porcine skin. The cathode patch configuration is as follows: 3 wt % Agarose+150 mM $CuCl_2$(⅛")/C/Ag Printed Ink/3 wt % Agarose+150 mM $CuCl_2$(¼")/Anion Exchange Membrane, ESC-7001/3 wt % Agarose+150 mM NaCl (⅛"). The exposed electrode area was 2 $cm^2$ and the operating current density was 0.2 $mA/cm^2$. The test was run for 24 hours at room temperature. The single electrode potential data was monitored with a Ag/AgCl wire reference electrode and recorded using a Fluke data logger. Unless otherwise stated all the voltage data described will be versus Ag/AgCl as the reference. Four (N=4) repeat experiments were run to determine reproducibility.

The data suggests good reproducibility with the four runs. In general the cathode potential decreases from 0 to ~−125 mV within the first 2–3 hours and then remains relatively constant for the remainder of the test period (21–22 hours). It must be noted that the cathode polarization is stable, low and reproducible suggesting good electrode performance over the 24 hour period.

The primary electrochemical reaction at the cathode is the reduction of $Cu^{2+}$ to Cu as given by:

$$Cu^{2+} + 2e^- \rightarrow Cu \qquad (10\text{-}1)$$

The decrease observed in the electrode polarization during the initial period can be explained by the transition in the electrochemistry form one electron to two electron reduction of copper ion.

At the end of the experiment, the porcine skin under the cathode compartment was analyzed for copper concentration using atomic absorption spectroscopy. For baseline purposes, a sample of fresh unused porcine skin was also simultaneously analyzed. The results of the copper ion concentrations in the cathode porcine skin are presented in Table 10-1. As seen from Table 10-1 the copper ion concentration in the fresh unused skin was <5 ppm and in the cathode skin was 13 ppm demonstrating the anion exchange membrane blocking substantial transport of the copper cations from the cathode compartment to the skin. pH measurements were also done at the end of the experiment on the electrode surface and on the gel surfaces in the electrode compartment. No detrimental pH effects were observed and the pH was measured to be 5.

TABLE 10-1

Copper ion concentration data in in-vitro skin with C/Ag printed ink cathode & copper chloride electrolyte.

|  | Concentration (ppm) |
|---|---|
| Fresh unused skin | <5 |
| Cathode skin 1 | 12 |
| Cathode skin 2 | 14 |
| Cathode skin 3 | 15 |
| Cathode skin 4 | 11 |

EXAMPLE 7

The objective of the following example is to determine the in vitro electrode/patch performance of a carbon coated silver cathode using a $CuSO_4$ electrolyte of the present invention. The experimental test set-up for this example is the as the experimental test set-up for Example 1.

Figure 11:
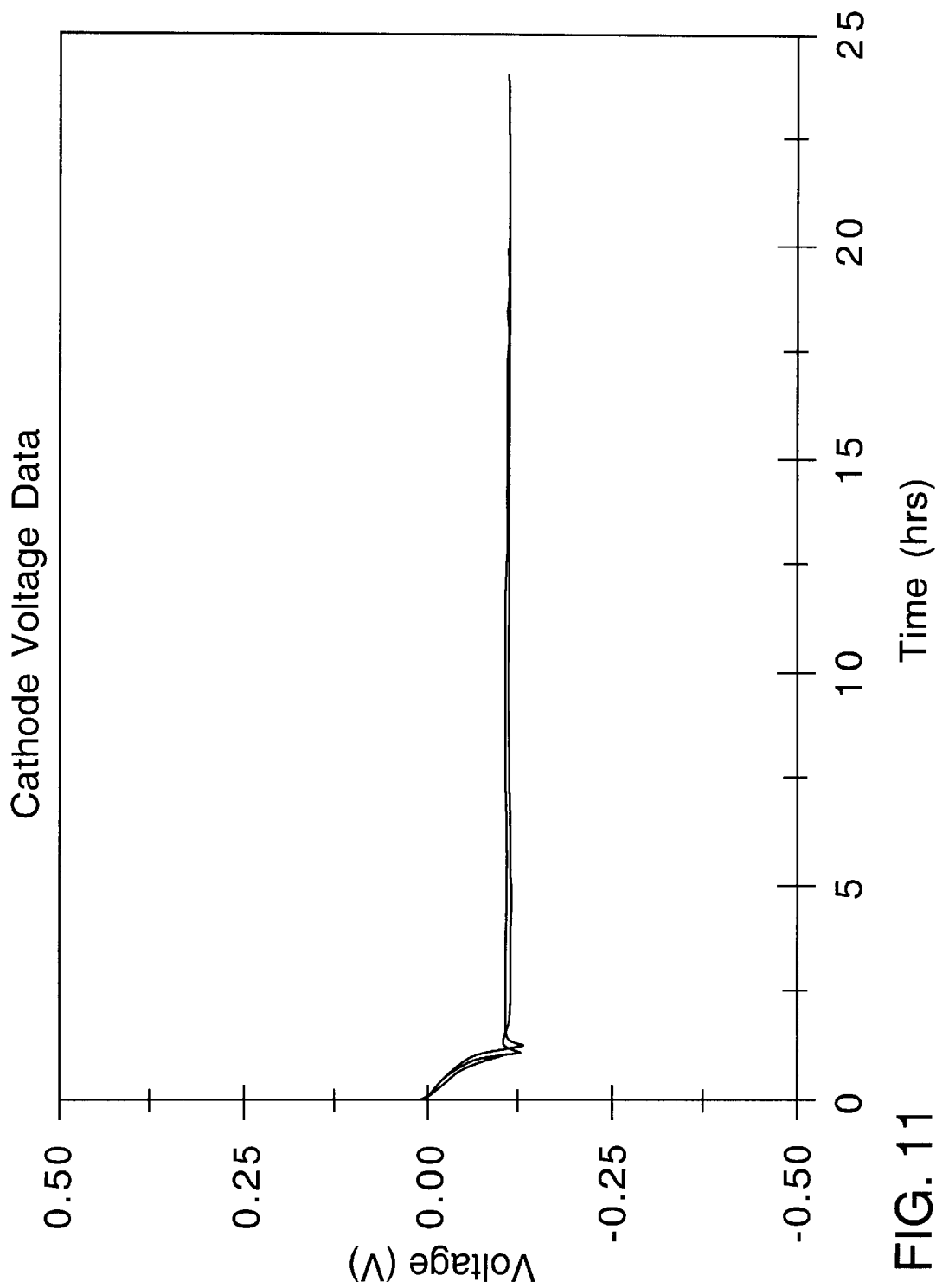
FIG. 11. is a graph illustrating in vitro performance data of a carbon coated silver cathode in an electrolyte containing $CuSO_4$.

FIG. 11 presents cathode performance data in patch configuration obtained with carbon coated silver cathode and copper sulfate electrolyte on the standard in-vitro test platform using excised porcine skin. The cathode patch configuration is as follows: 3 wt % Agarose+150 mM $CuSO_4$(⅛")/C/Ag Printed Ink/3 wt % Agarose+150 mM $CuSO_4$(¼")/Anion Exchange Membrane, ESC-7001/3 wt % Agarose+150 mM NaCl (⅛"). The exposed electrode area was 2 $cm^2$ and the operating current density was 0.2 $mA/cm^2$. The test was run for 24 hours at room temperature. The single electrode potential data was monitored with a Ag/AgCl wire reference electrode and recorded using a Fluke data logger. Unless otherwise stated all the voltage data described will be versus Ag/AgCl as the reference. Four (N=4) repeat experiments were run to determine reproducibility.

The data suggests good reproducibility with the four runs. In general the cathode potential decreases from 0 to ~−125 mV within the first 1–2 hours and then remains relatively constant for the remainder of the test period (22–23 hours). It must be noted that the cathode polarization is stable, low and reproducible suggesting good electrode performance over the 24 hour period. The primary electrochemical reaction at the cathode is the reduction of $Cu^{2+}$ to Cu as given by:

$$Cu^{2+} + 2e^- \rightarrow Cu \qquad (11\text{-}1)$$

At the end of the experiment, the porcine skin under the cathode compartment was analyzed for copper concentration using atomic absorption spectroscopy. For baseline purposes, a sample of fresh unused porcine skin was also simultaneously analyzed. The results of the copper ion concentrations in the cathode porcine skin are presented in Table 11-1. As seen from Table 11-1 the copper ion concentration in the fresh unused skin was <5 ppm and in the cathode skin was 77 ppm demonstrating the anion exchange membrane blocking substantial transport of the copper cations from the cathode compartment to the skin.

pH measurements were also done at the end of the experiment on the electrode surface and on the gel surfaces in the electrode compartment. No detrimental pH effects were observed and the pH was measured to be 5.

TABLE 11-1

Copper ion concentration data in in-vitro skin with C/Ag printed ink cathode & copper sulfate electrolyte.

|  | Concentration (ppm) |
|---|---|
| Fresh unused skin | <5 |
| Cathode skin 1 | 43 |
| Cathode skin 2 | 71 |
| Cathode skin 3 | 87 |
| Cathode skin 4 | 105 |

EXAMPLE 8

The following example provides a general description of how each of the in vivo examples were run using various embodiments of the present invention. Each examples 9 through 11 will provide information specifically directed to the type of anode, cathode, electrolyte, ion regulating mean or compartment separator used therein.

As indicated below this (in vivo) Example 8 was run using a traditional silver anode, silver chloride cathode and sodium chloride electrolyte. The objective of this example is to determine the electrode/patch performance of different electrochemical configurations by monitoring potentials, pH effects, electrochemical deposition and ion transport.

Figure 12:
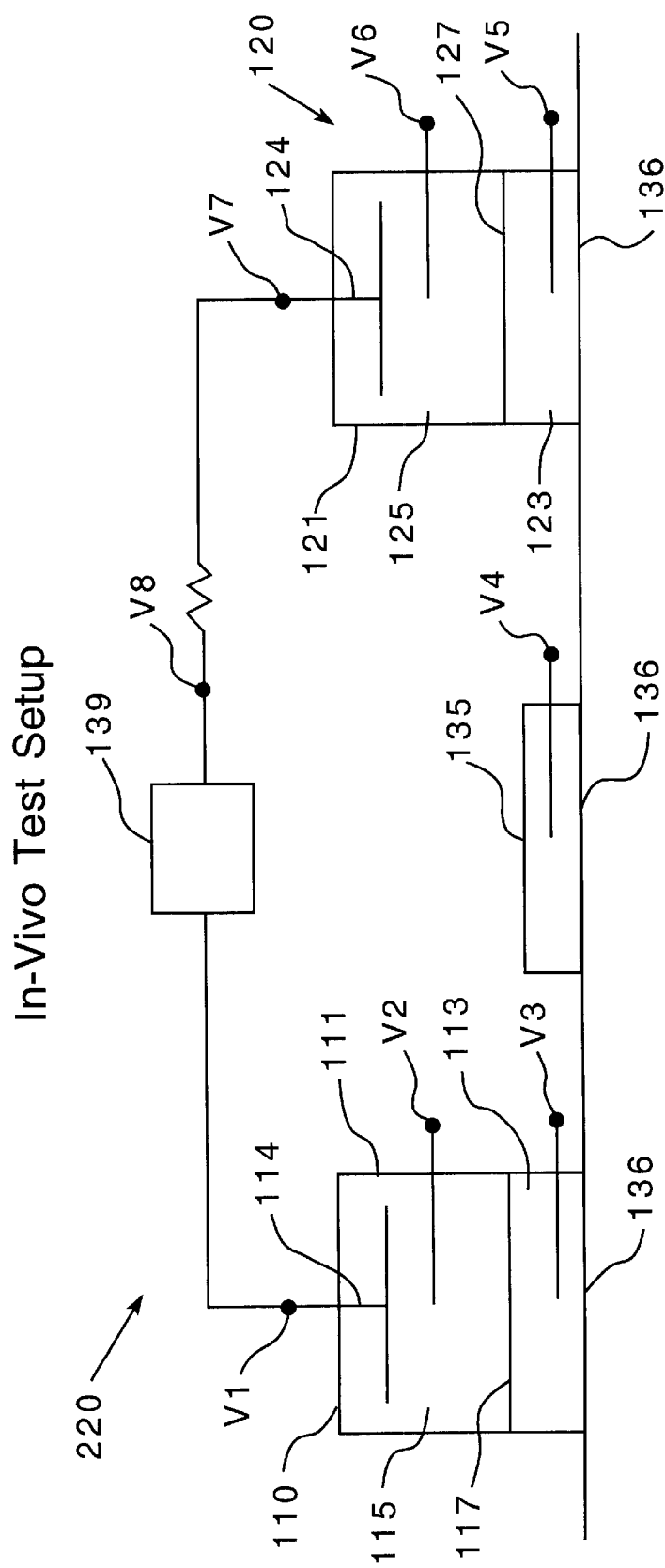
FIG. 12 depicts a test set up for in vivo 24 hour test of patch.

As depicted in FIG. 12 the in vivo test device 220 is configured as follows: an anode patch 110, having an anode electrode compartment 111 in ionic communication with a skin contacting compartment 113. The skin contacting compartment 113 and the anode electrode compartment 111 are separated by a compartment separation means 117. The anode electrode compartment 111 also contains an anode 114 and an electrolyte (anolyte) 115. The skin contacting compartment is attached to the rabbit skin 136. A cathode patch 120, having a cathode electrode compartment 121 in ionic communication with a skin contacting compartment 123. The skin contacting compartment 123 and the cathode electrode compartment 121 are separated by a compartment separation means 127. The cathode electrode compartment 121 also contains an cathode 124 and an electrolyte (catholyte) 125. The skin contacting compartment is attached to the rabbit skin 136. In electrical communication with both the anode patch 110 and the cathode patch 120 of the in vivo test device 220 is a reference patch 135, which is attached to the rabbit skin 136 between the anode patch 110 and the cathode patch 120. The reference patch 135 contains a reference electrode and electrolyte (not shown).

The experimental setup for this example was as follows:

Objective

To determine the electrode/patch performance of different electrochemistry's/configurations by monitoring potentials, pH effects, electrochemical deposition, ion transport and skin irritation.

Experimental Setup

Materials
  Anode separator: YCO5 size exclusion membrane
  Cathode separator: AXM-7001 anion exchange membrane
  IRP69 cation exchange resin
  Seakem Gold Agarose
  Faisson Foam (1/8", 1/16", 1/32")
  BDTS Ag/AgCl wire reference
  Saline
  Electrode Material:
    Anode: 6Ag 10077 Delker Mesh
    p1 Cathode: chlorided 6Ag 10077 Delker Mesh
Equipment
  Power Supply
  250 ml, 500 ml beaker
  Microwave
  Voltmeter
  Rabbits
  Rabbit Controllers
  Rabbit Restrainer
  Controller Patch Cord Patch Preparation The patches 110 and 120 are constructed with the appropriate faisson foams, separators, BDTS Ag/AgCl references, and electrodes for the electrode system that you are trying to study. The integrated patch is equipped with a nine pin connector so that a patch cord can be connected for ease of voltage measurements.

Solution Preparation

To prepare the electrolyte 115 and 125, make a mixture of the desired amount of Agarose with the electrolyte of interest (see below for examples). The mixture is heated until the Agarose is in solution. This is usually indicated by a color change from murky to clear. In the cases where IRP69 is in solution, heat until the solution is boiling.

Examples of Common Solutions
  Anolyte: 3 wt % Agarose+25 wt % IRP69 +10 mM NaCl
  Catholyte: 3 wt % Agarose+150 mM NaCl
  Reference Electrolyte: 3 wt % Agarose+150 mM NaCl
  Anode Skin Compartment: 3 wt % Agarose+10 mM NaCl
  Cathode Skin Compartment: 3 wt % Agarose/150 mM NaCl Loading Electrolyte into Patch The prepared electrolyte 115, 125 is loaded into the appropriate patch compartment 111, 121, respectively and allowed to cool. Seal the anode 114, cathode 124, and skin contacting compartment 113, 123 by placing a 3M acrylic adhesive film over the top of the compartment. This will reduce $H_2O$ loss due to evaporation in the patch 110, 120.

Preparing the Rabbit

A binocular patch (test device 220) is placed in position on the shaved smooth skin of the rabbit 136, and the controller is placed on the rabbit's back and taped in place. The positive lead of the controller is clipped onto the anode electrode 114 and the negative lead is clipped onto the cathode electrode 124. The rabbit is placed into a restraining cage and locked into place. The patch cord is attached to the patch.

Running the Experiment

Take a voltage measurement on the test device 220 before the current is turned on. Next, turn on the controller and take another voltage measurement. Voltage measurements are taken intermittently throughout the experiment. Next connect the monitoring device (not shown in FIG.) to the patch to measure electrode potentials (anode V1–V2, cathode V7–V6); separator voltages (anode V2–V3, cathode V5–V6); skin voltages (anode V3–V4, cathode V4–V5); and resistor voltage (V7–V8). While placing pressure on the electrodes one at a time and simultaneously taking voltage measurements a determination can be made with respect to the quality of the patch contact. If the voltage fluctuation is more than 500 mV, would indicate that the patch contact is poor.

Ending the Experiment

At the end of the 24th hour of running time, the power supply is turned off and the monitoring device is removed from the patches. The different compartments of the patch are then separated. The pH changes in the patch are measured. The gels are extracted to measure the electrolyte salt concentration, in this Example 8, $Na^+$ and Cl— concentrations are measured. In the case of a non Ag/AgCl system, the anode skin compartment and cathode skin compartment should be analyzed for metal ion content. Immediately upon removal of the patch, skin irritation should be measured using the Draise scale. Measure skin irritation again after 1 hour, 4 hours, and 1 day following completion of the 24 hr. run.

Data Analysis

Figure 13:
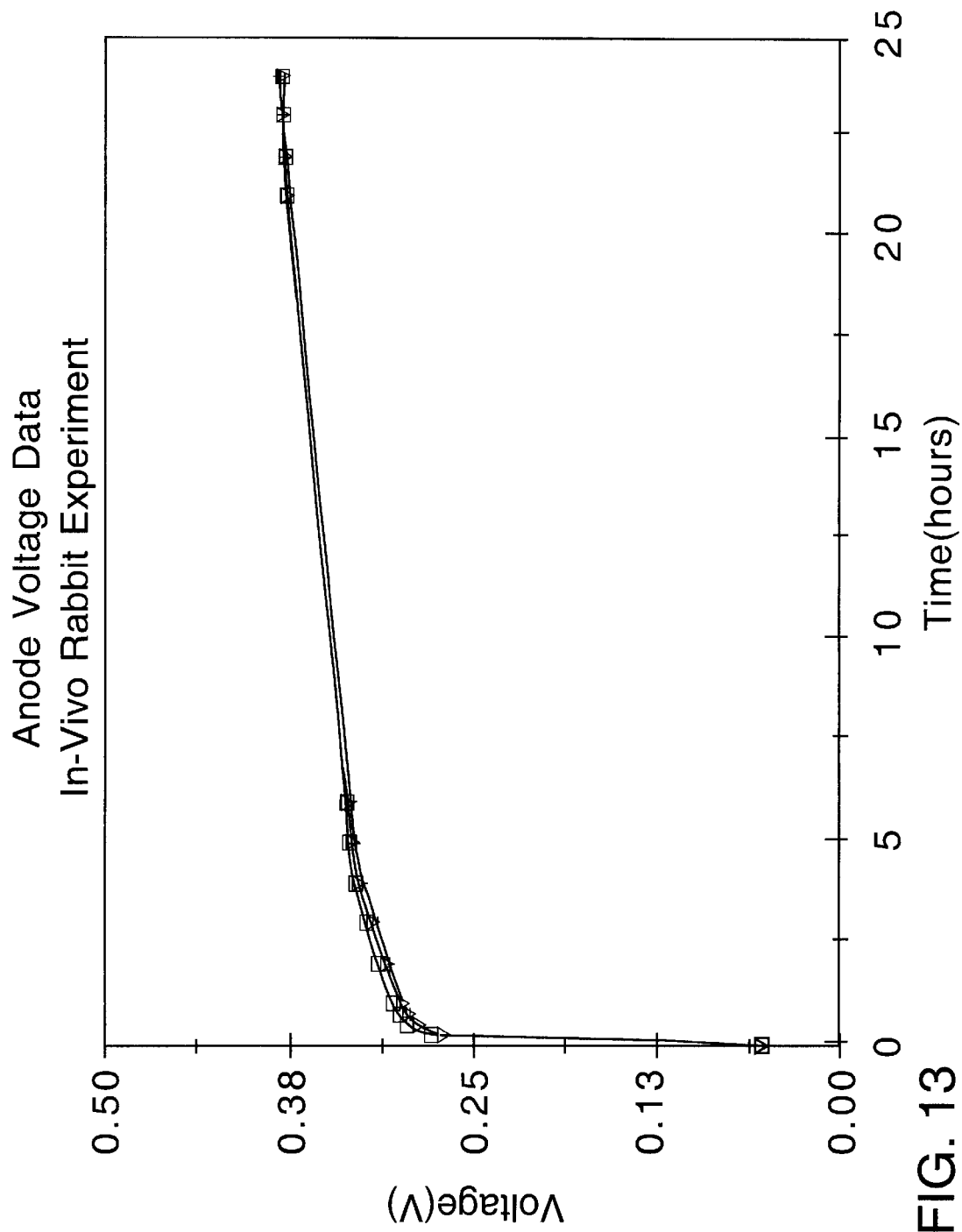
FIG. 13 is a graph illustrating in vivo performance data of a silver anode.
Figure 14:
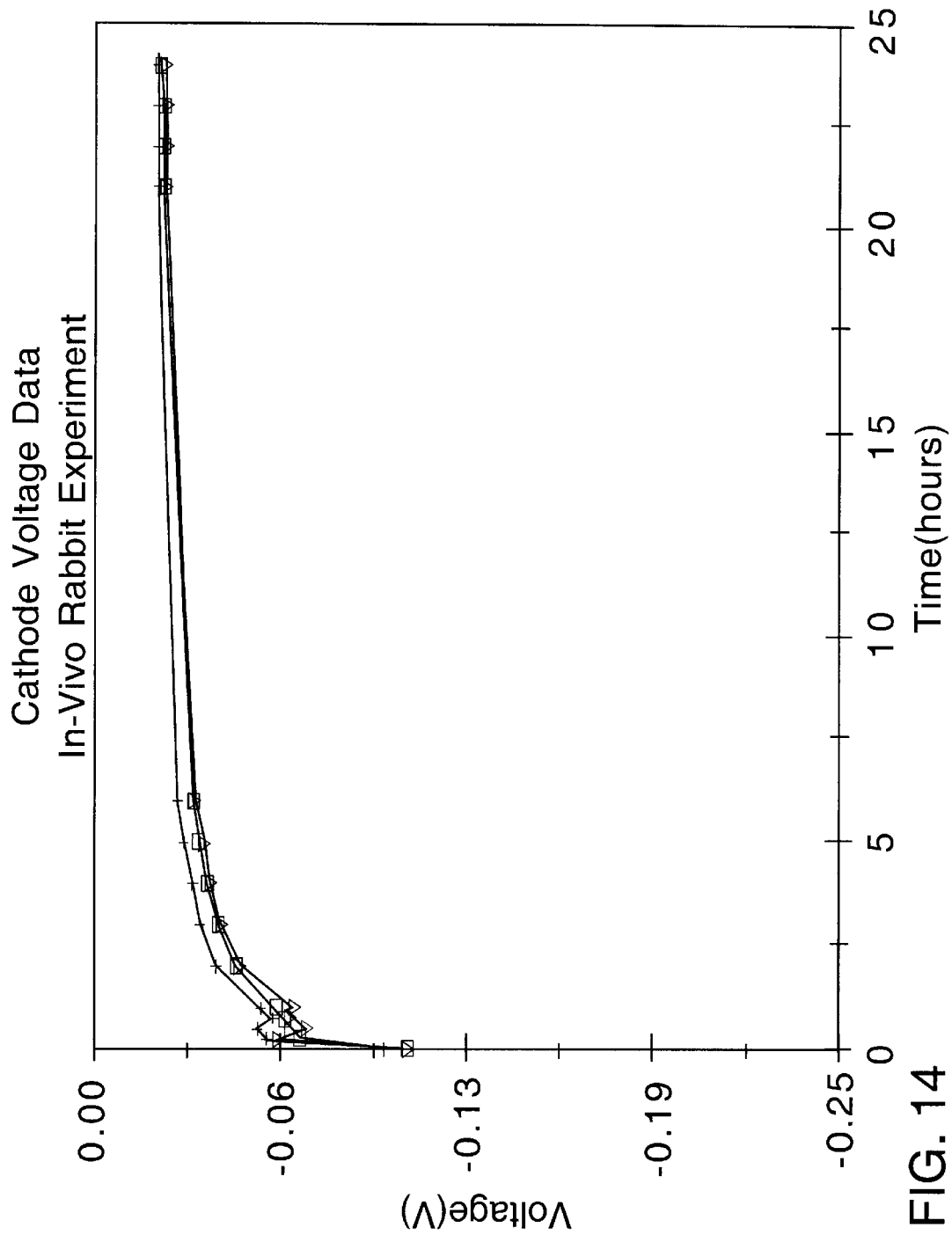
FIG. 14 is a graph illustrating in vivo performance data of a silver chloride cathode

FIGS. 13 and 14 illustrate electrode performance data in patch configuration obtained with the traditional Ag anode FIG. 13 and AgCl cathode FIG. 14 on the standard in vivo test platform using live rabbits. Details of the patch and the test conditions have been described above. The anode was formed from a silver Delker mesh (6Ag 10077) and the cathode was formed from a silver Delker mesh coated with silver chloride (chlorided 6Ag 10077). Additionally, the cathode electrolyte comprised 150 mM NaCl saline plus 3 wt. % agarose. The test was run for a period of 24 hrs and at a current density of 0.4 $mA/cm^2$. Three (N=3) repeat experiments were run to determine reproducibility.

The data suggests good reproducibility with the three runs. The in vivo data electrode performance is very similar to the in vitro data. In general the polarizations were found to be stable, low, and reproducible suggesting good electrode performance over the 24 hr. period. The primary anode electrochemical reaction is the dissolution of silver to silver ions and the primary cathode reaction is the reduction of silver chloride to silver.

pH measurements were also done at the end of the experiment on the electrode surface and on the gel surfaces in the electrode compartment. No detrimental pH effects were observed and the pH was measured to be 5–6.

At the end of the experiment, after the patches were removed from the animal, the skin under the patch was examined and scored for irritation (edema/eryhema) effects using the draize scoring scales. In general the draize scores were in the range of 0 to 2 immediately following completeion of the 24 hr test. However, the irritation effects dissappeared within twenty-four hours following the end of the test, suggesting the irritation effects to be of a transient nature.

EXAMPLE 9

The objective of the following example is to determine the in vivo electrode/patch performance of a silver coated copper anode of the present invention. The experimental test set-up for this example is the as the experimental test set-up for Example 8.

Figure 15:
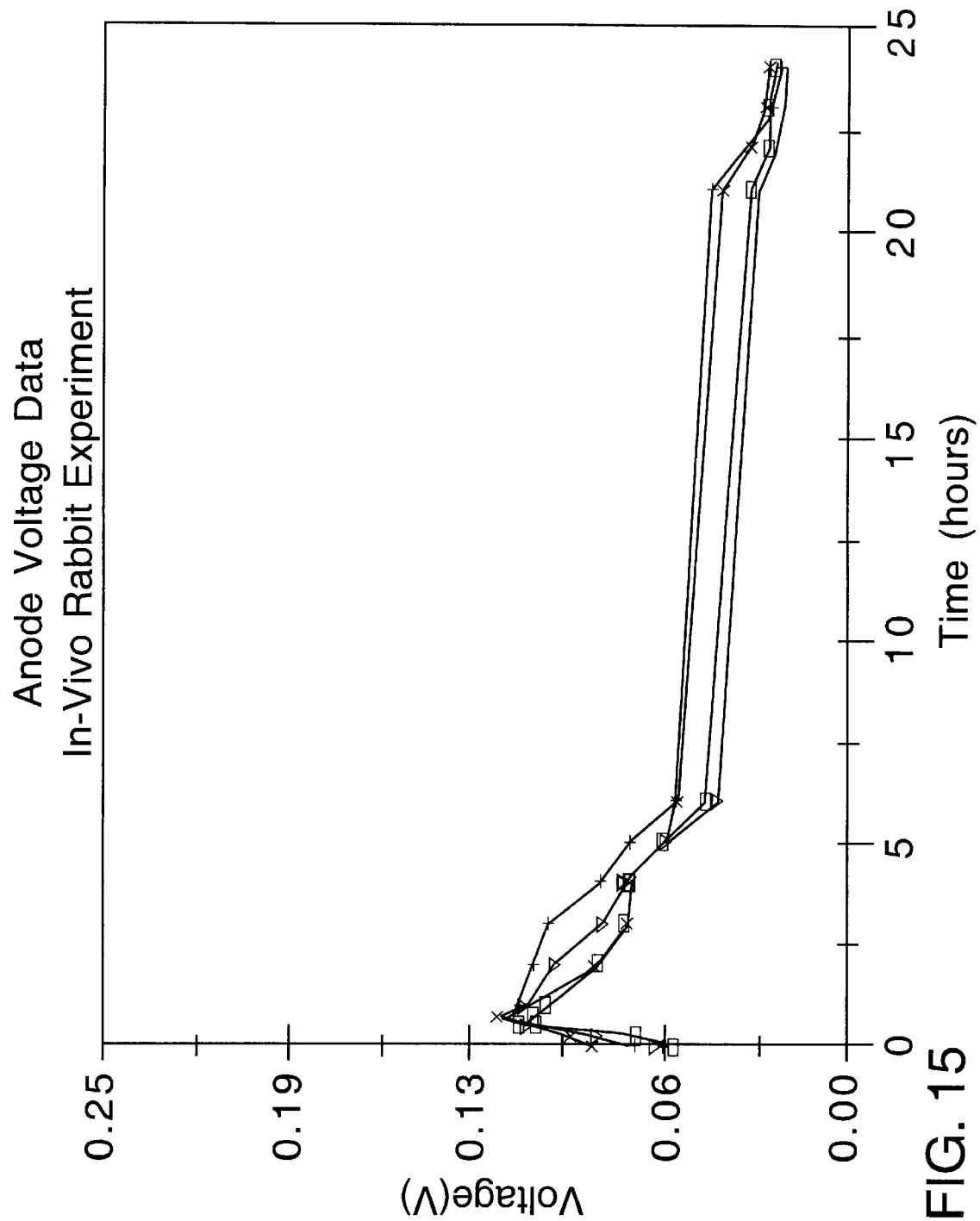
FIG. 15 is a graph illustrating in vivo performance data of a silver-coated copper anode of the present invention.

FIG. 15 presents anode performance data in patch configuration obtained with silver coated copper (Ag/Cu) anodes on standard in-vivo test platform using live rabbits. The anode patch configuration is as follows: 3 wt % Agarose+25 wt % IRP69 +10 mM NaCl (1/32")/"0.1 mil" Ag Coated 4Cu7-100 Delker Mesh/3 wt % Agarose+25 wt % IRP69+10 mM NaCl (1/4")/YCO5 Size Exclusion Membrane/3 wt % Agarose+10 mM NaCl (1/8"). The exposed electrode area was 2 cm$^2$ and the operating current density was 0.2 mA/cm$^2$. The test was run for 24 hours at room temperature. The single electrode potential data was monitored with a Ag/AgCl wire reference electrode and recorded. Unless otherwise stated all the voltage data described will be versus Ag/AgCl as the reference. Four (N=4) repeat experiments were run to determine reproducibility.

The data suggests good reproducibility with the four runs. The in-vivo electrode performance data is very similar to the in-vitro data. In general the anode potential rises to a maximum (100–150 mV) within the first hour and then gradually decreases to a steady state value of ~40 mV in 5–6 hours and then remains relatively constant for the remainder of the test period (15–16 hours). It must be noted that the anode polarization is stable, low and reproducible suggesting good electrode performance over the 24 hour test period.

pH measurements were also done at the end of the experiment on the electrode surface and on the gel surfaces in the electrode compartment. No detrimental pH effects were observed and the pH was measured to be 6.

At the end of the experiment, after the patches were removed from the animal, the skin under the patch was examined and scored for irritation (edema/eryhema) effects using the draize scoring scales. The results of irritation scoring are presented in Table 15-1 and the data clearly demonstrates no irritation effects.

TABLE 15-1

Draize score results after 24 hr of iontophoresis with Ag/Cu anode.

| Skin Irritation | Erythema | Edema |
|---|---|---|
| Anode 1 | 0 | 0 |
| Anode 2 | 0 | 0 |

TABLE 15-1-continued

Draize score results after 24 hr of iontophoresis with Ag/Cu anode.

| Skin Irritation | Erythema | Edema |
|---|---|---|
| Anode 3 | 0 | 0 |
| Anode 4 | 0 | 0 |

EXAMPLE 10

The objective of the following example is to determine the in vivo electrode/patch performance of an aluminum anode of the present invention. The experimental test set-up for this example is the as the experimental test set-up for Example 8.

Figure 16:
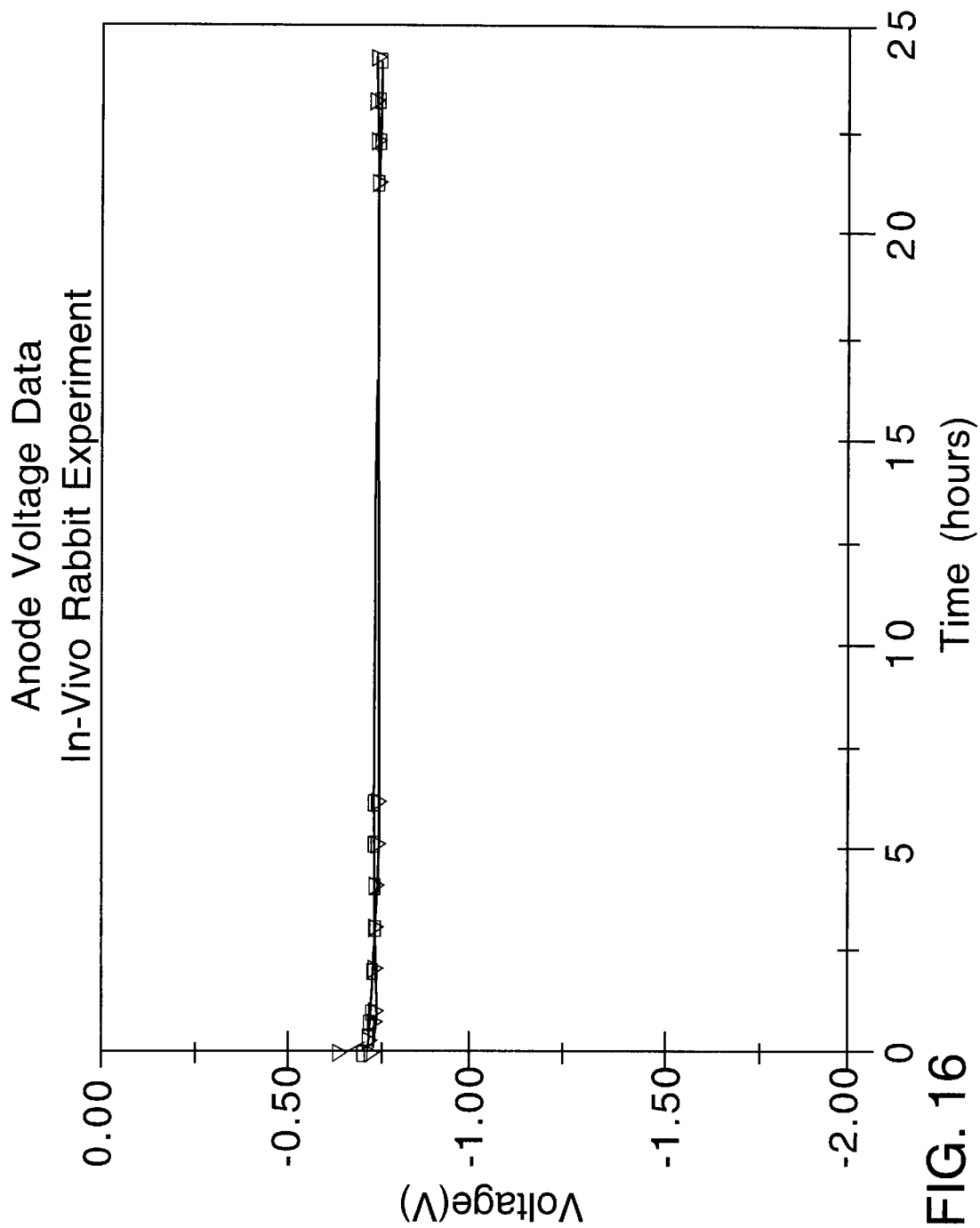
FIG. 16 is a graph illustrating in vivo performance data of an aluminum anode of the present invention.

FIG. 16 presents anode performance data in patch configuration obtained with Aluminum anodes on the standard in-vivo test platform using live rabbits. The anode patch configuration is as follows: 3 wt % Agarose+25 wt % IRP69+10 mM NaCl (1/32")/4A18-100 Delker Mesh/3 wt % Agarose+25 wt % IRP69+10 mM NaCl (1/4")/YCO5 Size Exclusion Membrane/3 wt % Agarose+10 mM NaCl (1/18"). The exposed electrode area was 2 cm$^2$ and the operating current density was 0.2 mA/cm$^2$. The test was run for 24 hours at room temperature. The single electrode potential data was monitored with a Ag/AgCl wire reference electrode. Unless otherwise stated all the voltage data described will be versus Ag/AgCl as the reference. Two (N=2) repeat experiments were run to determine reproducibility.

The data suggests excellent reproducibility with the two runs. The anode potential is relatively stable and flat at ~–0.75V over the entire 24 hours of test suggesting stable reproducible performance. The in-vivo electrode performance is very similar to the in-vitro data. The polarizations of the aluminum electrode are low suggesting good electrode performance.

pH measurements were also done at the end of the experiment on the electrode surface and on the gel surfaces in the electrode compartment. No detrimental pH effects were observed and the pH was measured to be 6.

At the end of the experiment, after the patches were removed from the animal, the skin under the patch was examined and scored for irritation (edema/erythema) effects using the draize scoring scales. The results of irritation scoring are presented in Table 16-1 and the data clearly demonstrates no irritation effects.

TABLE 16-1

Draize score results after 24 hr of iontophoresis with Aluminum anode.

| Skin Irritation | Erythema | Edema |
|---|---|---|
| Anode 1 | 0 | 0 |
| Anode 2 | 0 | 0 |

EXAMPLE 11

The objective of the following example is to determine the in vivo electrode/patch performance of a carbon coated silver cathode using a $ZnCl_2$ electrolyte of the present invention. The experimental test set-up for this example is the as the experimental test set-up for Example 8.

Figure 17:
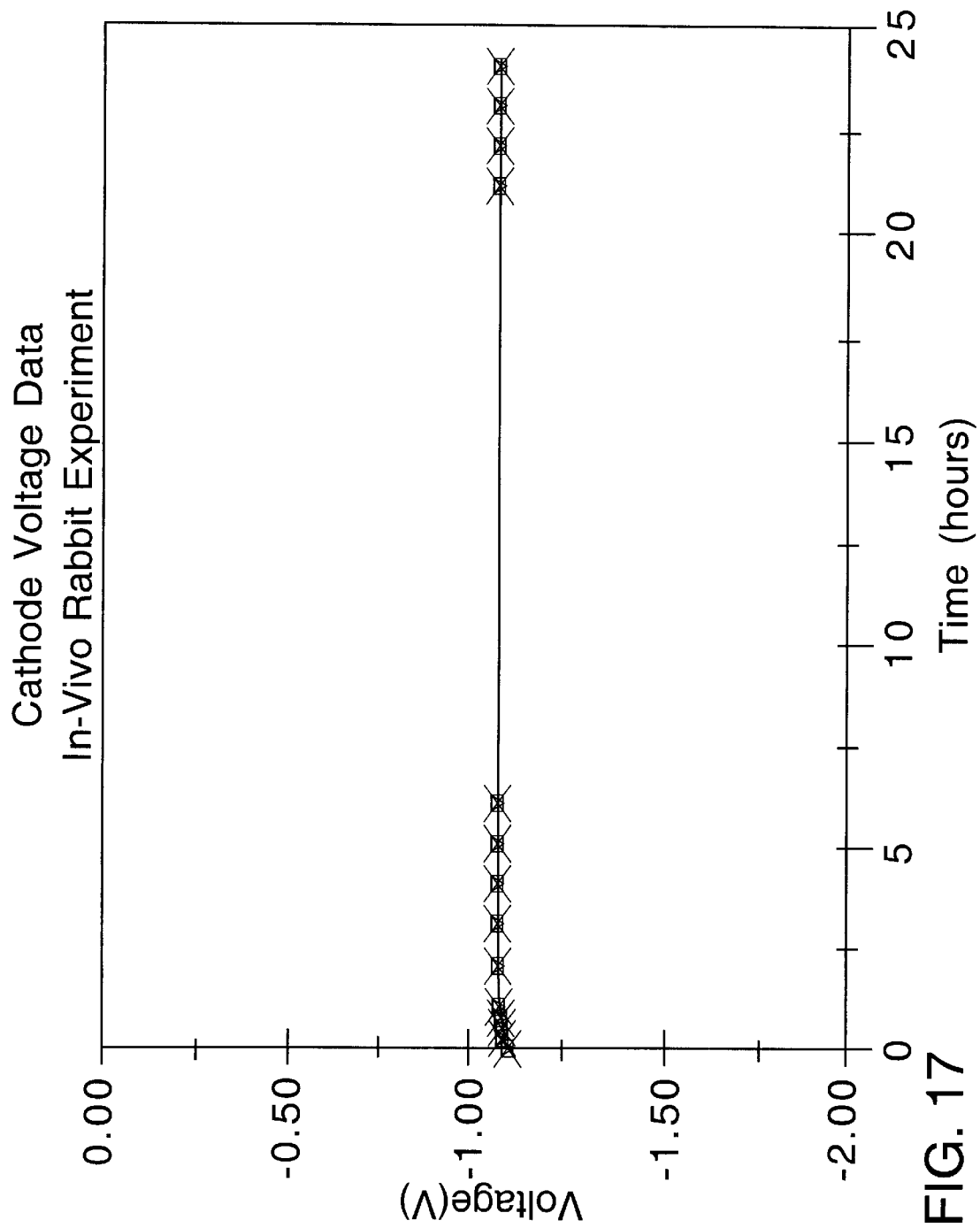
FIG. 17 is a graph illustrating in vivo performance data of a carbon coated silver cathode in an electrolyte containing $ZnCl_2$.

FIG. 17 presents cathode performance data in patch configuration obtained with carbon coated silver cathode and zinc chloride electrolyte on the standard in-vivo test platform using live rabbits. The cathode patch configuration is as follows: 3 wt % Agarose+150 mM ZnCl$_2$ (1/8")/C/Ag Printed Ink/3 wt % Agarose+150 mM ZnCl$_2$ (1/4")/Anion Exchange Membrane, ESC-7001/3 wt % Agarose+150 mM NaCl (1/8"). The exposed electrode area was 2 cm$^2$ and the operating current density was 0.2 mA/cm$^2$. The test was run for 24 hours at room temperature. The single electrode potential data was monitored with a Ag/AgCl wire reference electrode. Unless otherwise stated all the voltage data described will be versus Ag/AgCl as the reference. Four (N=4) repeat experiments were run to determine reproducibility.

The data suggests good reproducibility with the four runs. The cathode potential is relatively stable and flat at ~−1.1V over the entire 24 hours suggesting stable reproducible performance. The in-vivo electrode performance is very similar to the in-vitro data. The polarization at the cathode is very low suggesting good electrode performance.

pH measurements were also done at the end of the experiment on the electrode surface and on the gel surfaces in the electrode compartment. No detrimental pH effects were observed and the pH was measured to be 5.

At the end of the experiment, after the patches were removed from the animal, the skin under the patch was examined and scored for irritation (edema/erythema) effects using the draize scoring scales. The results of irritation scoring are presented in Table 17-1 and the data clearly demonstrates no irritation effects.

TABLE 17-1

Draize score results after 24 hr of iontophoresis with C/Ag cathode and zinc chloride electrolyte.

| Skin Irritation | Erythema | Edema |
| --- | --- | --- |
| Cathode 1 | 0 | 0 |
| Cathode 2 | 0 | 0 |
| Cathode 3 | 0 | 0 |
| Cathode 4 | 0 | 0 |

EXAMPLE 12 EFFECT OF IRP BEAD LOADING

To determine the effect of cation exchange bead loading in regulating the transport of metal ions generated at the anode, in-vitro iontophoresis experiments were done with Ag/Cu anodes as described in FIG. 6 with different bead loading in the anode compartments. The porcine skin was analyzed at the end of the experiment for copper content to determine the effect of bead loading in regulating copper ion transport to the skin. The patch configuration, setup, conditions and the procedure for all the tests is as described in FIG. 6. To vary the bead loading, the thickness of the anode compartments below the electrode was varied 1/4" to 1/16". Three patches (N=3) were run with 1/4" thick anode compartment, four (N=4) with 1/8" thick anode compartment and four (N=4) with 1/16" thick anode compartment. The anode performance data with all the patches were similar to those observed in FIG. 6.

The data for the analysis of the copper content in the porcine skin at the end of the experiment is presented in Table 18. The fresh unused skin had no copper in it (<5 ppm, below detection limits). With 1/4" thick compartment no copper was detected in the skin (<5 ppm, below detection limits) clearly demonstrating the effective trapping of the copper ions generated at the anode by the cation exchange beads and preventing them from reaching the skin. However, as the thickness of the anode compartment was reduced to 1/8" and 1/16" (hence lowering the bead loading), increasing amounts of finite copper amounts were detected in the skin after iontophoresis (11 ppm with 1/8" thick compartment and 56 ppm with 1/16" thick compartment). The data clearly demonstrates the role played by the beads in regulating the transport of metal cations generated at the electrode form reaching the skin surface.

TABLE 18

Copper concentration data (ppm) in porcine skin after 24 hour iontophoresis with Ag/Cu anodes and different bead loading.

| | 1/4" thick Anode Cpt | 1/8" thick Anode Cpt | 1/16" thick Anode Cpt |
| --- | --- | --- | --- |
| Fresh unused skin | <5 | <5 | <5 |
| Anode skin 1 | <5 | 11 | 75 |
| Anode skin 2 | <5 | 8 | 49 |
| Anode skin 3 | <5 | 15 | 57 |
| Anode skin 4 | | 9 | 41 |
| Anode skin average | <5 | 10.75 | 55.5 |

The electrode system and overall iontophoretic drug delivery device of the present invention is simple in construction allowing for ease of manufacture and is preferably formed from relatively inexpensive materials making the device economical. The electrode system includes an anode fabricated predominantly from a non-precious, base metal and a cathode fabricated on a flexible polymeric material using inks such as silver and carbon ink. These electrode systems are extremely cost-effective and have illustrated good voltage characteristics for use in an iontophoretic device.

The iontophoretic device of the present invention also overcomes several other disadvantages of known devices including reducing/eliminating pH burns and tattooing. Burns caused by changes in pH at the skin have been eliminated in the design of the present invention by preventing proton electrochemistry altogether. The system is operated at a voltage below that which causes proton electrochemistry, i.e. electrolysis of water, and the measured over voltages of the electrode systems are low and stable Tattooing has been avoided through the use of an ion exchange means in the electrolyte of the anode to capture metal ions produced therein and prevent the metal ions from entering the drug compartment and ultimately the skin of the patient.

Thus, the iontophoretic drug delivery system including the low-cost electrode system of the present invention provides significant advantages over presently available devices. It is economical, easy to manufacture, efficient, convenient to use and safe.

Although the illustrative embodiments of the present invention have been described with reference to the accompanying drawings, it is be understood that the invention is not limited to those precise embodiments, and that various other changed and modifications may be made by those skilled in the art without departing from the scope or spirit of the invention.

We claim:

1. An anode electrode for an iontophoretic device useful for delivering a medicament comprising:

an electrode compartment, said electrode compartment including an electrolyte comprising a medicament and an anode electrode in electrical communication with said electrolyte, said anode electrode including:

at least two electrochemically active, dissimilar metals such that a first chemically inert metal provides a coating having a thickness of about 0.1 mil over a second metal, said chemically inert first metal substantially preventing a chemical reaction of said second metal with said electrolyte containing said medicament during shelf storage and a skin contacting compartment which is in ionic communication with said electrode compartment; and an ion exchange material selected to capture positive ions of said second metal liberated by an electrochemical reaction during a use of said iontophoretic device to deliver said medicament, wherein said chemically inert first metal is substantially removed during said electrochemical reaction during an initial use of said device, said second metal thereby serving as the active electrode during subsequent delivery of said medicament.

2. An anode electrode as defined in claim 1, where the first metal comprises a precious metal and the second metal comprises a base metal wherein the anode electrode is fabricated from the base metal selected from the group consisting of iron, aluminum, tin, copper, zinc, nickel, brass, metal alloys and mixtures thereof, and wherein said precious metal coating serves to prevent said base metal from reacting with said electrolyte when said anode electrode is in electrical communication with said electrolyte and not in use, thereby prolonging the shelf-life of the anode electrode.

3. An anode electrode as defined in claim 2, wherein the anode electrode is in a form selected from the group consisting of: printed ink on polymeric film, mesh, laminate and foil.

4. An anode electrode as defined in claim 1 wherein the second metal is expanded copper foil mesh and the first metal is silver.

5. A cathode electrode disosed in an electrode compartment comprising an ion exchange material, said cathode electrode comprising a first chemically inert electron conductor material coated to a thickness of about 0.1 mil over a second electron conductive material and wherein said chemically inert electron conductor first material is present in a sufficient quantity to inhibit interaction between an electrolyte present in said electrode compartment during shelf storage and said cathode electrode, and wherein said first material is substantially removed when an electrical potential sufficient to induce an iontophoretic current is applied to said cathode electrode thereby exposing said second material for electrochemical activity wherein said chemically inert electron conductive first material is selected from the group consisting of carbon, silver, platinum and gold.

6. A cathode of claim 5 wherein said electron conductive second material is selected from the group consisting of silver, copper, aluminum, zinc, iron, gold, platinum, conductive polymers, conductive ceramics and conductive adhesives and is different from said chemically inert first electron conductive material.

7. A cathode electrode of claim 6 wherein said electron conductive material is selected from the group consisting of printed ink on polymeric film, mesh, laminate and foil.

8. An iontophoretic device useful for delivery of a drug comprises:

an anode electrode having an electrode compartment, said electrode compartment including an electrolyte comprising a medicament and an anode electrode in electrical communication with said electrolyte, said anode electrode including at least two electrochemically active, dissimilar metals such that a first chemically inert metal disposed as a coating having a thickness of about 0.1 mil over a second metal, said chemically inert first metal substantially preventing a chemical reaction of said second metal with said electrolyte during shelf storage and a skin contacting compartment which is in ionic communication with said electrode compartment including an ion exchange material selected to capture positive ions of said second metal liberated by an electrochemical reaction during a use of said iontophoretic device to deliver said medicament, wherein said chemically inert first metal is substantially removed during said electrochemical reaction during initial use of said device, said second metal thereby serving as the active electrode during subsequent delivery of said medicament;

a cathode patch having a electrode compartment, said cathode electrode compartment including an electrolyte and a cathode electrode comprising chemically inert electron conductive first material coated on an electron conductive second material, different from said first material, said electrolyte including an ionizable reducible metal salt capable of being reduced at said cathode electrode and a cathode skin contacting compartment, the skin contacting compartment including an electrolyte for ionically contacting the skin of the patient, the skin compartment being ionically connected to said cathode electrode compartment and wherein said cathode electrode compartment further includes an ion selective material for substantially preventing ions of said reducible metal salt from migration into said cathode skin contacting compartment;

a power source electrically connected to said anode patch and said cathode patch so that when said anode patch and said cathode patch are disposed on the skin of a patient thereby forming a complete circuit capable of supporting an iontophoretic current between said patches through said patient's skin so that when at least one of said cathode patch and said anode patch further includes a suitable medicament, said medicament is delivered into the skin of the patient.

9. A method for substantially preventing a destructive interaction during shelf storage between an electrolyte comprising a medicament and an electrode in an iontophoretic drug delivery device useful for delivering the medicament comprising:

providing an electrode having an electrode compartment;

providing an electrolyte comprising a medicament;

placing said electrolyte comprising said medicament in said electrode compartment;

providing a skin contacting compartment in ionic communication with said electrode compartment;

forming an electrode from a first electrochemically active metal capable of forming metallic ions in an electrochemical reaction;

selecting an ion exchange material capable of binding said metallic ions formed from said first electrochemically active metal;

placing said ion exchange material in one of said skin contacting compartment and said electrode compartment;

selecting another electrochemically active metal, different from said first metal and substantially inert when in contact with said electrolyte comprising said medicament;

applying said second electrochemically active metal as a coating having a thickness about 0.1 mil, over said electrode formed from said first electrochemically active metal; and placing said electrode having said coating thereon in said electrode compartment in electrical communication with said electrolyte comprising said medicament, thereby providing said electrode having said chemically inert first metal substantially for substantially preventing a chemical reaction of said second metal with said electrolyte comprising said medicament during shelf storage of said device, said chemically inert first metal being substantially removed during an electrochemical reaction during an initial use of said device, said second metal thereby serving as the active electrode during subsequent delivery of said medicament.

10. An anode electrode for an iontophoretic medicament delivery device comprising:

an electrode compartment including an electrolyte comprising a medicament and an anode electrode in electrical communication with said electrolyte, said anode electrode including copper having an outside surface, said surface having a coating with a thickness of about 0.1 mil of silver thereon, said silver substantially preventing a chemical reaction between said copper and said electrolyte containing said medicament during shelf storage;

a skin contacting compartment which is in ionic communication with said electrode compartment; and an ion exchange material selected to capture positive ions of said copper liberated by an electrochemical reaction during a use of said iontophoretic device to deliver said medicament, wherein said chemically inert first metal is substantially removed during said electrochemical reaction during an initial use of said device, said copper thereby serving as the active electrode during subsequent iontophoretic delivery of said medicament.

11. A cathode electrode for an iontophoretic delivery device comprising:

an electrode compartment including an electrolyte and a cathode electrode comprising carbon coated on silver, said electrolyte including an ionizable reducible metal salt capable of being reduced at said cathode electrode; and a skin contacting compartment, the skin contacting compartment including an electrolyte for ionically contacting the skin of the patient, the skin compartment being ionically connected to said electrode compartment and wherein said electrode compartment further includes an ion selective material for substantially preventing ions of said reducible metal salt from migration into said skin contacting compartment.

12. An iontophoretic drug delivery device comprising:

an anode electrode comprising an electrode compartment including an electrolyte comprising a medicament and an anode electrode in electrical communication with said electrolyte, said anode electrode including copper having an outside surface, said surface having a coating with a thickness of about 0.1 mil of silver thereon, said silver substantially preventing a chemical reaction between said copper and said electrolyte containing said medicament during shelf storage;

a skin contacting compartment in ionic communication with said electrode compartment;

an ion exchange material selected to capture positive ions of said copper liberated by an electrochemical reaction during a use of said iontophoretic device to deliver said medicament, wherein said chemically inert first metal is substantially removed during said electrochemical reaction during an initial use of said device, said copper thereby serving as the active electrode during subsequent iontophoretic delivery of said medicament;

a cathode electrode comprising an electrode compartment including an electrolyte and a cathode electrode comprising carbon coated on silver, said electrolyte including an ionizable reducible metal salt capable of being reduced at said cathode electrode;

a skin contacting compartment, the skin contacting compartment including an electrolyte for ionically contacting the skin of the patient, the skin compartment being ionically connected to said electrode compartment and wherein said electrode compartment further includes an ion selective material for substantially preventing ions of said reducible metal salt from migration into said skin contacting compartment; and a suitable power source connected to said anode electrode and said cathode electrode so that when said anode electrode and said cathode electrode are placed in ionic contact with the skin of a patient, a completed electrical circuit is established between said anode and said cathode so that said medicament is transported from said anode into said patient's skin.

13. An anode patch for an electrode assembly of an iontophoretic medicament delivery device, the device delivering the medicament over a time period, the patch comprising:

an electrode compartment, said electrode compartment comprising an electrolyte and an electrode which is in ionic communication with said electrolyte, said electrode comprising at least two dissimilar electrochemically active metals such that a first metal is a coating over a second metal, wherein said first metal substantially prevents a chemical reaction of said second metal with said electrolyte during storage, and wherein said first metal is substantially removed by an electrochemical reaction within about a first 10% of the time period during an initial use of said patch such that said second metal serves as the active electrode; and a skin contact compartment, said skin contact compartment in ionic communication with said electrode compartment.

14. The anode patch of claim 13 wherein said electrode is solid and substantially planar.

15. The anode patch of claim 13 wherein said electrode is selected from the group consisting of a foil, a laminate, and printed ink on polymeric film.

16. The anode patch of claim 13 wherein said electrode is an open mesh.

17. The anode patch of claim 16 wherein said open mesh is selected from the group consisting of woven, nonwoven screen, and expanded foil.

18. The anode patch of claim 13 wherein said electrode is formed by printed ink technology utilizing at least one technique selected from the group consisting of impression, lithography, offset, gravure, jet application, silk-screening, electroplating, and vacuum sputtering.

19. The anode patch of claim 13 wherein said skin contact compartment contains a medicament.

20. The anode patch of claim 13 further comprising a housing positioned on a surface of said electrode compartment.

21. The anode patch of claim 20 wherein said housing is made of a material selected from the group consisting of polymeric foam, plastic, polyvinyl chloride, and polyethylene.

22. The anode patch of claim 20 further comprising a backing film positioned on at least a part of said housing.

23. The anode patch of claim 13 further comprising a release liner positioned on an underside surface of said skin contact compartment.

24. The anode patch of claim 13 wherein said second metal is selected from the group consisting of a non-precious metal and an electrically conductive metal composite.

25. The anode patch of claim 24 wherein said second metal is selected from the group consisting of aluminum, tin, zinc, copper, nickel, brass, iron, silver, and alloys of any of aluminum, tin, zinc, copper, nickel, brass, iron, and silver.

26. The anode patch of claim 13 wherein said first metal is selected from the group consisting of a precious metal and a chemically inert metal.

27. The anode patch of claim 26 wherein said first metal is silver.

28. The anode patch of claim 13 further comprising an ion regulating material in ionic communication with said electrolyte and said electrode.

29. The anode patch of claim 28 wherein said ion regulating material is between said electrode and said skin contact compartment.

30. The anode patch of claim 29 wherein said ion regulating material is an anion exchange material.

31. The anode patch of claim 13 wherein said electrolyte comprises a hydrogel matrix including saline.

32. The anode patch of claim 31 further comprising an ion regulating material distributed in said matrix.

33. The anode patch of claim 32 wherein said ion regulating material is a cation exchange material.

34. The anode patch of claim 13 further comprising a compartment separation material between said electrode compartment and said skin contact compartment.

35. The anode patch of claim 34 wherein said compartment separation material is a size exclusion membrane.

36. The anode patch of claim 13 wherein said skin contact compartment includes a material selected from the group consisting of a solid material, a semi-solid material, a polymeric film, a semi-permeable membrane, a differentially permeable membrane, a hydrogel, and a microporous membrane.

37. The anode patch of claim 13, wherein said skin contact compartment includes agarose.

38. The anode patch of claim 13 wherein said first metal is silver and said second metal is copper.

39. The anode patch of claim 13 wherein said electrode includes an expanded copper foil mesh.

40. An iontophoretic device useful for iontophoretically delivering a medicament comprising:
the anode patch of claim 13; and
a cathode patch.

41. A cathode patch for an electrode assembly of an iontophoretic medicament delivery device, the patch comprising:
an electrode compartment, said electrode compartment comprising an electrolyte and an electrode in ionic communication with said electrolyte, said electrode comprising at least two materials such that a first material is a coating over a second material, said first material being carbon and said second material being selected from the group consisting of copper, silver, and aluminum, wherein said first material substantially prevents a chemical reaction of said second material with said electrolyte during storage, and wherein, during use, said materials are not consumed, and said electrode serves as an active electrode; and
a skin contact compartment, said skin contact compartment in ionic communication with said electrode compartment.

42. The cathode patch of claim 41 further comprising a compartment separation material between said electrode compartment and said skin contact compartment.

43. The cathode patch of claim 41 wherein said electrode is in solid substantially planar form.

44. The cathode patch of claim 41 wherein said electrode is selected from the group consisting of printed ink on polymeric film, a foil, and a laminate.

45. The cathode patch of claim 41 wherein said electrode is an open mesh.

46. The cathode patch of claim 45 wherein said open mesh is selected from the group consisting of woven, nonwoven screen, and expanded foil.

47. The cathode patch of claim 41 wherein said electrode is formed by printed ink technology utilizing at least one technique selected from the group consisting of impression, lithography, offset, gravure, jet application, silk-screening, electroplating, and vacuum sputtering.

48. The cathode patch of claim 41 wherein said skin contact compartment contains a medicament.

49. The cathode patch of claim 41 further comprising a housing positioned on a surface of said electrode compartment.

50. The cathode patch of claim 49 wherein said housing is made of a material selected from the group consisting of polymeric foam, plastic, polyvinyl chloride, and polyethylene.

51. The cathode patch of claim 41 further comprising a backing film positioned on at least a part of said housing.

52. The cathode patch of claim 41 further comprising a release liner positioned on an underside surface of said skin contact compartment.

53. The cathode patch of claim 41 wherein said second material is capable of conducting electrons.

54. The cathode patch of claim 41 wherein said first material is chemically inert and capable of conducting electrons.

55. The cathode patch of claim 41 wherein said electrolyte comprises a soluble, ionizable, reducible metal salt.

56. The cathode patch of claim 55 wherein said salt is selected from the group consisting of copper chloride, copper nitrate, copper sulfate, silver nitrate, zinc chloride, zinc nitrate, zinc sulfate, iron chloride, iron nitrate, and iron sulfate.

57. The cathode patch of claim 41 further comprising an ion regulating material in ionic communication with said electrolyte and said electrode.

58. The cathode patch of claim 57 wherein said ion regulating material is between said electrode compartment and said skin contact compartment.

59. The cathode patch of claim 58 wherein said ion regulating material is selected from the group consisting of an anion exchange membrane and anion exchange beads.

60. The cathode patch of claim 41 wherein said patch is fabricated on a thin flexible polymeric film.

61. The cathode patch of claim 41 wherein said patch comprises an expanded copper foil mesh.

62. The cathode patch of claim 41 wherein said first material is carbon and said second material is silver.

63. The cathode patch of claim 62 wherein said electrolyte of said patch is selected from the group consisting of a $ZnCl_2$ solution, a $ZnSO_4$ solution, a $CuCl_2$ solution, and a $CuSO_4$ solution.

64. An iontophoretic device useful for iontophoretically delivering a medicament comprising:
an anode patch; and
the cathode patch of claim 41.

65. An iontophoretic device useful for iontophoretically delivering a medicament, the device delivering the medicament over a time period, comprising:
an anode patch comprising
a first electrode compartment, said first electrode compartment comprising a first electrolyte and a first electrode in ionic communication with said first electrolyte, said first electrode comprising at least two dissimilar electrochemically active metals such that a first metal is a coating over a second metal, wherein said first metal substantially prevents a chemical reaction of said second metal with said first electrolyte during storage, and wherein said first metal is substantially removed by an electrochemical reaction within about a first 10% of the time period during an initial use of said patch such that said second metal serves as an active electrode, and a first skin contact compartment, said first skin contact compartment in ionic communication with said first electrode compartment;

a cathode patch comprising a second electrode compartment, said second electrode compartment comprising a second electrolyte and a second electrode in ionic communication with said second electrolyte, said second electrode comprising at least two materials such that a first material is a coating over a second material, wherein said first material substantially prevents a chemical reaction of said second material with said second electrolyte during storage, and wherein, during use, said materials are not consumed, and said electrode serves as an active electrode; and a second skin contact compartment, said second skin contact compartment in ionic communication with said second electrode compartment; and a power source electrically connected to said anode patch and said cathode patch.

66. The iontophoretic device of claim 65 further comprising a medicament.

67. The iontophoretic device of claim 66 wherein said medicament is located in said first skin contact compartment.

68. The iontophoretic device of claim 67 wherein said medicament has a positive charge in solution.

69. The iontophoretic device of claim 66 wherein said medicament is located in said second skin contact compartment.

70. The iontophoretic device of claim 69 wherein said medicament has a negative charge in solution.

71. The iontophoretic device of claim 65 wherein, in use, said anode patch and said cathode patch are disposed on the skin of a patient, thereby forming a complete circuit capable of supporting an iontophoretic current between said anode patch and said cathode patch through said skin so that said medicament is delivered into said skin.

72. The iontophoretic device of claim 71 wherein said anode patch and said cathode patch form a galvanic couple.

73. An anode patch for an electrode assembly of an iontophoretic medicament delivery device, the device delivering the medicament over a time period, the patch comprising:

an electrode compartment, said electrode compartment comprising an electrolyte and an electrode which is in ionic communication with said electrolyte, said electrode comprising at least two dissimilar electrochemically active metals such that a first metal is a coating over a second metal, wherein said first metal substantially prevents a chemical reaction of said second metal with said electrolyte during storage, and wherein said first metal is substantially removed by an electrochemical reaction within about a first 10% of the time period during an initial use of said patch such that said second metal serves as the active electrode; and a skin contact compartment, said skin contact compartment in ionic communication with said electrode compartment.

74. The iontophoretic device of claim 73, wherein said skin contact compartment further comprises a drug.

75. An iontophoretic device useful for iontophoretically delivering a medicament over a time period, comprising:

an anode patch comprising a first electrode compartment, said first electrode compartment comprising a first electrolyte and a first electrode in ionic communication with said first electrolyte, said first electrode comprising at least two dissimilar electrochemically active metals such that a first metal is a coating over a second metal, wherein said first metal substantially prevents a chemical reaction of said second metal with said first electrolyte during storage, and wherein said first metal is substantially removed by an electrochemical reaction within about a first 10% of the time period during an initial use of said patch such that said second metal serves as an active electrode, and a first skin contact compartment, said first skin contact compartment in ionic communication with said first electrode compartment;

a cathode patch comprising a second electrode compartment, said second electrode compartment comprising a second electrolyte and a second electrode in ionic communication with said second electrolyte, said second electrode comprising at least two materials such that a first material is a coating over a second material, wherein said first material substantially prevents a chemical reaction of said second material with said second electrolyte during storage, and wherein, during use, said materials are not consumed, and said electrode serves as an active electrode; and a second skin contact compartment, said second skin contact compartment in ionic communication with said second electrode compartment; and a power source electrically connected to said anode patch and said cathode patch.

76. The iontophoretic device of claim 75, wherein said first skin contact compartment further comprises a drug.

77. The iontophoretic device of claim 75, wherein said second skin contact compartment further comprises a drug.

* * * * *

UNITED STATES PATENT AND TRADEMARK OFFICE
CERTIFICATE OF CORRECTION

PATENT NO.    : 6,584,349 B1
DATED         : June 24, 2003
INVENTOR(S)   : Sage et al.

It is certified that error appears in the above-identified patent and that said Letters Patent is hereby corrected as shown below:

Title page,
Item [75], Inventors, delete "John R. DeNuzzio" and substitute therefore -- John D. DeNuzzio --.
Item [56], References Cited, U.S. PATENT DOCUMENTS, Ariura et al. insert -- U.S. Patent 4,474,570, 10/1984, --

Column 2,
Line 65, delete "not use" and substitute therefor -- not in use --.

Column 3,
Line 31, delete "limitation aluminum" and substitute therefor -- limitation, aluminum --.
Line 56, before "drug" delete "-- contact is of --".

Column 7,
Line 1, delete "containing a an ion" and substitute therefor -- containing an ion --.

Column 8,
Line 34, delete "Feb. 2, 1997" and substitute therefor -- Feb. 2, 1993 --.
Lines 34-35, delete "disclosurue" and substitute therefore -- disclosure --.

Column 9,
Lines 29-30, delete "This is material" and substitute therefor -- This material --.

Column 14,
Line 30, delete "is the as" and substitute therefore -- is the same as --.

Column 15,
Line 49, delete "is the as" and substitute therefore -- is the same as --.

Column 16,
Line 66-67, delete "is the as" and substitute therefore -- is the same as --.

Column 17,
Lines 60-61, delete "is the as" and substitute therefore -- is the same as --.

Column 18,
Lines 54-55, delete "is the as" and substitute therefore -- is the same as --.

UNITED STATES PATENT AND TRADEMARK OFFICE
CERTIFICATE OF CORRECTION

PATENT NO. : 6,584,349 B1
DATED : June 24, 2003
INVENTOR(S) : Sage et al.

It is certified that error appears in the above-identified patent and that said Letters Patent is hereby corrected as shown below:

Column 19,
Line 19, delete "form" and substitute therefor -- from --.

Column 24,
Line 15, delete "is the as" and substitute therefore -- is the same as --.
Lines 64-65, delete "is the as" and substitute therefore -- is the same as --.

Column 27,
Line 36, delete "disosed" and substitute therefor -- disposed --.

Signed and Sealed this

Sixteenth Day of November, 2004

JON W. DUDAS
*Director of the United States Patent and Trademark Office*